(12) United States Patent
Whitcombe et al.

(10) Patent No.: US 6,326,145 B1
(45) Date of Patent: Dec. 4, 2001

(54) METHODS FOR DETECTING TARGET NUCLEIC ACID SEQUENCES

(75) Inventors: David Mark Whitcombe; Jane Theaker; Neil James Gibson; Stephen Little, all of Northwich (GB)

(73) Assignee: Zeneca Limited (GB)

( * ) Notice: Subject to any disclaimer, the term of this patent is extended or adjusted under 35 U.S.C. 154(b) by 0 days.

(21) Appl. No.: 09/200,232

(22) Filed: Nov. 25, 1998

(30) Foreign Application Priority Data

Jun. 13, 1998 (GB) .................................................. 9812768

(51) Int. Cl.[7] .............................. C12Q 1/68; C12P 19/34; C07H 21/02; C07H 23/00
(52) U.S. Cl. ......................... 435/6; 435/91.1; 435/91.2; 536/23.1; 536/25.4; 536/26.42
(58) Field of Search ........................... 435/91.2, 6, 91.1; 536/24.3, 23.1, 25.4, 26.42

(56) References Cited

U.S. PATENT DOCUMENTS

| | | | |
|---|---|---|---|
| 4,996,143 | 2/1991 | Heller et al. | 435/6 |
| 5,118,801 | 6/1992 | Lizardi et al. | 536/27 |
| 5,210,015 | 5/1993 | Gelfand et al. | 435/6 |
| 5,312,728 | 5/1994 | Lizardi et al. | 435/6 |
| 5,525,494 | 6/1996 | Newton | 435/91.2 |
| 5,532,129 | 7/1996 | Heller | 435/6 |
| 5,538,848 | 7/1996 | Livak et al. | 435/5 |
| 5,565,322 | 10/1996 | Heller | 435/6 |
| 5,573,906 | 11/1996 | Bannwarth et al. | 435/6 |
| 5,593,840 * | 1/1997 | Bhatnagar et al. | 435/6 |
| 5,595,890 | 1/1997 | Newton et al. | 435/91.2 |
| 5,607,834 | 3/1997 | Bagwell | 435/6 |
| 5,691,146 | 11/1997 | Mayrand | 435/6 |
| 5,723,591 | 3/1998 | Livak et al. | 536/22.1 |
| 5,804,375 | 9/1998 | Gelfand et al. | 435/6 |
| 5,866,336 | 2/1999 | Nazarenko et al. | 435/6 |
| 5,876,930 | 3/1999 | Livak et al. | 435/6 |
| 5,919,630 | 7/1999 | Nadeau et al. | 435/6 |
| 5,925,517 | 7/1999 | Tyagi et al. | 435/6 |
| 5,935,791 | 8/1999 | Nadeau et al. | 435/6 |

FOREIGN PATENT DOCUMENTS

| | | | |
|---|---|---|---|
| 0229943 | 7/1987 | (EP) | C12Q/1/68 |
| 0232967 | 8/1987 | (EP) | C12Q/1/68 |
| 0416817 | 3/1991 | (EP) | C12Q/1/68 |
| 0566751 | 10/1993 | (EP) | C12Q/1/68 |

(List continued on next page.)

OTHER PUBLICATIONS

Cantor, "Lighting Up Hybridization," *Nature Biotechnology*, 14:247 (Mar. 1999).

(List continued on next page.)

*Primary Examiner*—Jeffrey Fredman
*Assistant Examiner*—Joyce Tung
(74) *Attorney, Agent, or Firm*—Rothwell, Figg, Ernst & Manbeck

(57) ABSTRACT

A method for the detection of a target nucleic acid, which method comprises contacting template nucleic acid from a sample with (i) a signalling system and (ii) a tailed nucleic acid primer having a template binding region and the tail comprising a linker and a target binding region, in the presence of appropriate nucleoside triphosphates and an agent for polymerization thereof, under conditions such that the template binding region of the primer will hybridize to a complementary sequence in the template nucleic acid and be extended to form a primer extension product, separating any such product from the template whereupon the target binding region in the tail of the primer will hybridize to a sequence in the primer extension product corresponding to the target nucleic acid, and wherein any such target specific hybridization causes a detectable change in the signalling system, such that the presence or absence of the target nucleic acid in the sample is detected by reference to the presence or absence of a detectable change in the signalling system.

9 Claims, 42 Drawing Sheets

FOREIGN PATENT DOCUMENTS

| | | | |
|---|---|---|---|
| 0436644 | 4/1996 | (EP) | C12Q/1/68 |
| 0745690 | 12/1996 | (EP) | C12Q/1/68 |
| 0881302 | 12/1998 | (EP) | C12Q/1/68 |
| 0909823 | 4/1999 | (EP) | C12Q/1/68 |
| 9818811 | 5/1998 | (WO) | C07H/21/02 |
| 9739008 | 10/1997 | (WO) | C07H/21/04 |
| 9745539 | 12/1997 | (WO) | C12N/15/11 |
| 9202638 | 2/1992 | (WO) | C12Q/1/68 |
| 9421820 | 9/1994 | (WO) | C12Q/1/68 |
| 9513399 | 5/1995 | (WO) | C12Q/1/68 |
| 9615270 | 5/1996 | (WO) | C12Q/1/68 |
| 9742345 | 11/1997 | (WO) | C12Q/1/68 |
| 9810096 | 3/1998 | (WO) | C12Q/1/68 |
| 9826093 | 6/1998 | (WO) | C12Q/1/68 |

OTHER PUBLICATIONS

Gibson et al., "A Homogeneous Method for Genotyping with Fluorescence Polarization," *Clinical Chemistry*, 43:8, pp. 1336–1341 (1997).

Nazarenko et al., "A Closed Tube Format for Amplification and Detection of DNA Based Energy Transfer," *Nucleic Acids Research*, 25:12, pp. 2516–2521 (1997).

Tyagi S. et al., "Molecular Beacons: Probes that Fluoresce upon Hybridization." *Nature Technology*, vol. 14, pp. 303–308 (Mar. 1, 1996).

Wilton et al., "Snapback SSCP Analysis: Engineered Conformation Changes for the Rapid Typing of Known Mutations," *Human Mutation*, vol. 11, pp. 252–258 (Mar. 1998).

Wittwer et al., "Continuous Fluorescence Monitoring of Rapid Cycle DNA Amplification," *Biotechniques*, 22:1, pp. 130–131/134–138, (Jan. 1997).

Yokoi et al., "Use of AmpliSensor to Quantitate Gene Expression in Small Amounts of Samples: Comparison with the Quantitative RT–PCR Method Using CCD Imaging System," *Japanese Journal of Clinical Pathology*, 44:9, pp. 847–852, (Sep. 1996).

* cited by examiner a.

b.

a.

b.

Capture sequence a.

b.

2-tube test

Single tube test

Probe matches target, fluorophore unquenched

OR

Probe and target mismatch, internally quenched conformation forms

OR

For allele "a" on the forward strand

OR

For allele "b" on the reverse strand

Allelic discrimination
on the upper strand

OR

PLUS

Amplicon control on
the other strand
using a second fluorophore

SEQUENCE LISTING

<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: B2098-BRCA
      Scorpions primer
<221> NAME/KEY: stem_loop
<222> LOCATION: (1)..(29)
<221> NAME/KEY: misc_feature
<222> LOCATION: (30)
<223> OTHER INFORMATION: n = MR = a non-fluorogenic fluorophore attached
      to a uracil
<221> NAME/KEY: misc_feature
<222> LOCATION: (31)
<223> OTHER INFORMATION: n = HEG = blocking hexethylene glycol monomer

<400> SEQUENCE: 1
cgcacgatgt agcacatcag aagcgtgcgn nttggagatt ttgtcacttc cactctcaaa        60

<210> SEQ ID NO 2
<211> LENGTH: 29

```
<212> TYPE: DNA
<213> ORGANISM: Artificial Sequence
<220> FEATURE:
<223> OTHER INFORMATION: Description of Artificial Sequence: R186-98,
      Untailed equivalent of B2098 primer

<400> SEQUENCE: 2
ttggagattt tgtcacttcc actctcaaa                                       29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Z3702,
      Probe segment of the Scorpions B2098 primer
<221> NAME/KEY: stem_loop
<222> LOCATION: (1)..(29)
<221> NAME/KEY: misc_feature
<222> LOCATION: (30)
<223> OTHER INFORMATION: n = MR = a non-fluorogenic fluorophore
      attached to a uracil

<400> SEQUENCE: 3
cgcacgatgt agcacatcag aagcgtgcgn                                      30

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: B2731
      Scorpion primer
<221> NAME/KEY: misc_feature
<222> LOCATION: (18)
<223> OTHER INFORMATION: n = MR = a non-fluorogenic fluorophore
      attached to a uracil
<221> NAME/KEY: misc_feature
<222> LOCATION: (19)
<223> OTHER INFORMATION: n = H = blocking hexethylene glycol monomer

<400> SEQUENCE: 4
aggtagtgca gagagtgnng agcctcaaca tcctgctccc ctcctactac                50

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: B4249
      Scorpion primer without quencher on same molecule
<221> NAME/KEY: misc_feature
<222> LOCATION: (18)
<223> OTHER INFORMATION: n = h = blocking hexethylene glycol monomer

<400> SEQUENCE: 5
aggtagtgca gagagtgnga gcctcaacat cctgctcccc tcctactac                 49

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Quencher
      oligonucleotide for B4249 (complement tail)
<221> NAME/KEY: misc_feature
<222> LOCATION: (18)
<223> OTHER INFORMATION: n = MR = a non-fluorogenic fluorophore
      attached to a uracil

<400> SEQUENCE: 6
```

```
cactctctgc actacctn                                                            18

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: ARMS primer
      R284-97

<400> SEQUENCE: 7
ttcggggctc cacacggcga ctctcaac                                                 28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: ARMS
      primer R283-97

<400> SEQUENCE: 8
ttcggggctc cacacggcga ctctcaag                                                 28
```

METHODS FOR DETECTING TARGET NUCLEIC ACID SEQUENCES

The present invention relates to a novel detection system comprising novel primers and an integrated signalling system. The system is used in the detection of target nucleic acid sequences.

Available methods for the amplification and detection of target nucleic acid sequences include use of the polymerase chain reaction (PCR), for example as described in U.S. Pat. Nos. 4,683,195 and 4,683,202.

A significant improvement on the above amplification and detection methods is the Amplification Refractory Mutation System (ARMS) as claimed in our European Patent no. 0 332 435 (Zeneca Limited) and corresponding U.S. Pat. No. 5,595,890.

Convenient probe based detection systems include Taqman (as disclosed in U.S. Pat. Nos. 5,210,015 and 5,487,972) and Molecular Beacons (as disclosed in WO-95/13399). In Taqman a probe molecule comprising fluorophore/quencher species hybridises to PCR amplification products and is digested by the 5'-3' exonuclease activity of a polymerase. This leads to release of unquenched fluorophore and a corresponding detectable signal. In Molecular Beacons a probe molecule having a stem-loop structure keeping fluorophore and quencher species in close proximity opens out upon binding to its complementary target whereupon the fluorophore becomes unquenched leading to a detectable signal.

Nazarenko et al (NAR 1997, 25, 2516–2521) disclose so called "Sunrise" primers. These are primers which form hairpin loops at their 5' ends to bring a fluorophore and quencher pair together, thus ensuring low fluorescence. When these primers have been incorporated into a PCR product, the tails become double stranded and the hairpin is unravelled causing the fluorescence to increase. However signal generation is not amplicon dependent, any double stranded amplicon (including primer dimers) can incorporate the Sunrise primer and thus generate a spurious signal.

U.S. Pat. No. 5,573,906 (Bannwarth et al) describe a process using a 5' labelled primer containing a self-complementary sequence in an amplification or extension process together with a subsequent detection step using a 3' labelled probe for the amplified or extended region. The labels may be close together in space after hybridising the probe close to the short piece of double-stranded DNA resulting from backfolding of the self-complementary region of the primer incorporated into the amplified or extended product.

However, the levels of sequence specificity and detection sensitivity, as well as speed of signal appearance, achievable using the above amplification and detection methods are limited. Therefore the need still exists for further improved diagnostic methods.

We have now devised a novel detection system using a tailed primer and an integrated signalling system. The primer has a template binding region and a tail comprising a linker and a target binding region. In use the target binding region in the tail hybridises to complementary sequence in an extension product of the primer. This target specific hybridisation event is coupled to a signalling system wherein hybridisation leads to a detectable change.

Therefore in a first aspect of the present invention we provide a method for the detection of a target nucleic acid, which method comprises contacting template nucleic acid from a sample with (i) a signalling system and (ii) a tailed nucleic acid primer having a template binding region and the tail comprising a linker and a target binding region, in the presence of appropriate nucleoside triphosphates and an agent for polymerisation thereof, under conditions such that the template binding region of the primer will hybridise to a complementary sequence in the template nucleic acid and be extended to form a primer extension product, separating any such product from the template whereupon the target binding region in the tail of the primer will hybridise to a sequence in the primer extension product corresponding to the target nucleic acid, and wherein any such target specific hybridisation causes a detectable change in the signalling system, such that the presence or absence of the target nucleic acid in the sample is detected by reference to the presence or absence of a detectable change in the signalling system.

The detection method of the invention has a number of significant advantages. These include the following. Only a single primer/detector species is required. This means simplicity and provides enhanced specificity based on the ready availability of the target binding region for hybridisation with the primer extension product. The newly synthesised primer extension product is the target species so the output signal obtainable is directly related to amount of extended primer. It is not dependent on additional hybridisation events or enzymatic steps (such as TaqMan cleavage). Intra- and inter-strand competition for the probe site is limited so probe design becomes simplified. We have found that probes which fail to bind under standard assay conditions in separate probe format work well in our invention. The invention also allows homogeneous assay formats to be readily devised. A still further advantage is that, as the interaction is unimolecular, the signalling reaction is very rapid, permitting increased cycling rates. This is a significant feature for assay designs.

Wilton et al (Human Mutation, 1998, 11, 252–258) disclose an analytical method termed Snapback Single Strand Conformation Polymorphism (SSCP). This involves the use of a tailed primer to introduce a secondary structure in a single strand of an amplicon. The primers consist of standard 3' ends with short tails on the 5' end. These tails are complementary to an internal region of the amplicon at some distance from the primer and can be used to probe the conformation of the single strands formed after heating and cooling. The conformational changes introduced by a mutation at the probe complementary site are detected by migration rate changeson a polyacylamide gel stained with silver. However there is no anticipation of the features or advantages of the present invention.

In the detection method of the invention, primer extension may be repeated one or more times such as up to 5, up to 10, up to 15, up to 20, up to 30, up to 40, up to 50 or more times. Conveniently, the novel primer of the invention is used as an amplification primer in an amplification system such as the polymerase chain reaction (PCR). In which case the target binding region and the tail region are advantageously arranged such that the tail region remains single stranded, ie. uncopied. Thus the tail region is non-amplifiable in the PCR amplification products. This facet of primer design is claimed in our European Patent No. 0 416 817 (Zeneca Limited) and corresponding U.S. Pat. No. 5,525,494. Conveniently the linker comprises a blocking moiety which prevents polymerase mediated chain extension on the primer template. A preferred blocking moiety is a hexethylene glycol (HEG) monomer. Alternatively the primer tail comprises material such as 2-O-alkyl RNA which will not permit polymerase mediated replication of a complementary strand. Alternatively the tail comprises nucleic acid placed 5'-3' at the 5' terminus of the primer ie. the two sequences are placed "back to back", it will be appreciated that in this embodiment the 5'-3' nucleic acid of the tail serves both as the linker and the target binding region. A separate and distinct linker moiety is not essential.

The template binding region of the primer hybridises to template nucleic acid from a sample. The region is of any convenient design available to the person of ordinary skill and is limited only by practical considerations. It may be DNA, RNA or other provided that it provides a substrate for polymerase mediated primer extension. Template binding can be effected at any desired stringency, that is to say under appropriate hybridisation stringency conditions the template binding region of the primer may hybridise to the template region (if present in the template) to the exclusion of other regions. Alternatively template binding may be effected at reduced stringency to extend the primer on any convenient number of related template sequences, such as for example human leukocyte antigen (HLA) genes, or other conserved genes, particularly bacterial or ribosomal RNA genes. Primers may be provided wherein the template binding regions are members of a set of random hexamer sequences. Thus the expression "a complementary sequence" is intended to include all sequences outlined above provided that the template binding region and hybridisation conditions allow the desired degree of sequence discrimination. By way of example the template binding region may be 100%, up to 95%, up to 90%, up to 85%, up to 80%, up to 75%, or up to 70% complementary to the corresponding template sequence. The template binding region is conveniently of 6–50 nucleotides such as 10–40 nucleotides, 15–30 nucleotides, particularly 20–30, 17–22, 16–23 or 15–24 nucleotides. Each of the above ranges is a separate and independent embodiment of the invention. All of the above applies in an analogous manner to the target binding region of the primer with the proviso that the target binding region is in general shorter that the template binding region, examples of convenient and preferred ranges are set out hereinafter. It will be appreciated that the overall selectivity of the method of the invention may be applied in an allele-specific or multiple allele manner for the template binding or target binding regions independently. Each permutation is a particular aspect of the invention.

As outlined above, the target binding region may if desired comprise a non-copiable species such as 2'-O-methyl RNA, peptide nucleic acid (PNA) and variants of these. In this case a separately identifiable linker is not required and the target binding region is considered to comprise a linker separating the template binding and target binding regions. The target binding region may be shorter than those traditionally designed for hybridisation to amplicons (amplification products) since the amplicon-target interactions of this invention are unimolecular and hence kinetically (and thermodynamically) more favoured than bi-molecular interactions. By way of non-limiting example, the target binding region may comprise no more than 6, such as no more than 7, no more than, 8 no more than 9 or no more than 10 nucleotides.

It will be understood that the tail of the primer may include additional nucleotides complementary to part of the template binding region in the primer. These may be used to "fine tune" the affinity of the primer tail for complementary sequences.

The linker separates the template binding and target binding regions. Optimum characteristics for the linker may be determined by routine experimentation. Whilst we do not wish to be bound by theoretical considerations, the linker may comprise no more than 200 nucleotides or less such as 100 or 50 nucleotides. In general these regions are kept close together, we believe this may favour hybridisation of target binding region to the target region. In a preferred aspect the linker comprises a non-amplifiable moiety such as HEG, alone or combined with further nucleotides, more preferably alone. Where the template binding region and the tail region of the primer are arranged to prevent polymerase-mediated copying of the primer tail the linker may be a direct bond.

In a further aspect of the invention we provide a nucleic acid primer comprising (i) a template binding region and (ii) a tail comprising a linker and a target binding region such that in use the target binding region hybridises to a complementary sequence in an extension product of the primer corresponding to the target nucleic acid. The template binding region and the tail region are preferably arranged such that the tail region remains single stranded in the PCR amplification products. More preferably a blocking moiety is sited between the template binding region of the primer and the tail region, which moiety prevents polymerase mediated chain copying of the tail region of the primer template. A particular blocking moiety is a hexethylene glycol (HEG) monomer. The target binding region is preferably selected to hybridise to a complementary target sequence in the primer extension product less than 200 such as less than 100 base pairs, such as less than 50 base pairs, such as less than 40 base pairs, less than 30 base pairs less than 25 or less than 20 base pairs such as less than 15, 10 or even 5 from a sequence complementary to the template binding region in the primer.

Hybridisation of the target binding region in the tail of the primer to a complementary sequence in the primer extension product corresponding to the target nucleic acid causes a detectable change in the signalling system. Any convenient signalling system may be used, by way of non-limiting example we refer to the measurement of the change in fluorescence polarisation of a fluorescently labelled species (European Patent No. 0 382 433-Zeneca Limited), DNA binding proteins, creation of restriction sites in duplex species for endpoint detection, the bringing together of elements to give a target site, the incorporation of detectably (modified) dNTPs into primer extension products and further probe species. In addition any convenient sequence specific species may be used, examples include intercalators such as wavelength specific intercalators, also species used to form triplex structures. Convenient intercalators will be apparent to the scientist skilled in the art (cf. Higuchi et al, BioTechnology, 1992, 10, 413–417).

Further systems include two-component systems where a signal is created or abolished when the two components are brought into close proximity with one another. Alternatively a signal is created or abolished when the two components are separated following binding of the target binding region.

Both elements of the two component system may be provided on the same or different molecules. By way of example the elements are placed on different molecules, target specific binding displaces one of the molecules into solution leading to a detectable signal.

Convenient two-component systems may based on the use of energy transfer, for example between a fluorophore and a quencher. In a particular aspect of the invention the detection system comprises a fluorophore/quencher pair. Convenient and preferred attachment points for energy transfer partners may be determined by routine experimentation. A number of convenient fluorophore/quencher pairs are detailed in the literature (for example Glazer et al, Current Opinion in Biotechnology, 1997, 8, 94–102) and in catalogues such as those from Molecular Probes, Glen and Applied Biosystems (ABI). Any fluorescent molecule is suitable for signalling provided it may be detected on the instrumentation available. Most preferred are those compatible with the 488 nm laser of the ABI PRISM 7700 (Fluorescein and Rhodamine derivatives). The quencher must be able to quench the dye in question and this may be via a Fluorescence Resonance Energy Transfer (FRET) mechanism involving a second, receptor fluorophore, or more preferably via a collisional mechanism involving a non-fluorogenic quencher such as DABCYL, which is a "Universal" quencher of fluorescence Furthermore it is preferred that the selected fluorophores and quenchers are easily incorporated into the oligonucleotide, most conveniently via phosphoramidite chemistry. Convenient donors include FAM, HEX and TET.

We surprisingly found that, without the inclusion of a specific quencher, the tail alone can provide sufficient quenching of fluorescence. When the target binding region hybridises to a complementary sequence in the primer extension product a clear fluorescence signal is observed. The optimum point of attachment of the fluorophore may determined by routine experimentation. In a further aspect of the invention the signalling system comprises a fluorophore attached to the tail region of the primer, conveniently at or adjacent the termini 5' terminus of the primer. Whilst we do not wish to be limited by theoretical considerations, any G-rich sequence of at least 5 base pairs, such as at least 10 or at least 15, such as at least 20 base pairs may be used as a quencher species.

In a further specific embodiment, the primer tail includes an intercalating dye, hybridisation of the target binding region causes the dye to become incorporated between the bases of the double stranded DNA and thus to fluoresce. The dye should preferably have a low fluorescence when not intercalated, and a strong fluorescent enhancement upon intercalation. Again the preferred molecules should be easy to attach to the oligonucleotide by solid phase chemistry or by simple post-synthesis addition.

It will be appreciated that the overall length of the primer tail will be determined principally by the intended functions of its individual components. In general, the primer tail will be of at least 10 base pairs, such as at least 20, 30, 40 or 50 base pairs, for example 10–30 or 15–25 base pairs.

It is desirable that all dyes, quenchers, linkers/blockers should tolerate repeated rounds of PCR which include multiple exposures to high temperatures.

In a preferred aspect of the invention at least one component of the signalling system and the nucleic acid primer is an integral species.

The template nucleic acid is any convenient nucleic acid for analysis. Most commonly this will be DNA from an amplification reaction such as the PCR. This DNA target may have been derived from a reverse transcription (RT) reaction. Indeed, the primer of the invention may be used in the RT reaction itself and be used directly, without further amplification. Other in vitro amplification techniques such as ligase chain reaction (LCR), OLA, NASBA and Strand Displacement Amplification (SDA) may also be suitable. It is important however that there is a single stranded intermediate which allows the target binding region to hybridise to a complementary sequence in the primer extension product. In general the method of our invention is used as the last (detection) step in the above methods. It will be appreciated that some optimisation/reconfiguration may be required but the relevant steps will be apparent to the artisan of ordinary skill.

Sources of sample nucleic acid include human cells such circulating blood, buccal epithelial cells, cultured cells and tumour cells. Also other mammalian tissue, blood and cultured cells are suitable sources of template nucleic acids. In addition, viruses, bacteriophage, bacteria, fungi and other micro-organisms can be the source of nucleic acid for analysis. The DNA may be genomic or it may be cloned in plasmids, bacteriophage, bacterial artificial chromosomes (BACs), yeast artificial chromosomes (YACs) or other vectors. RNA may be isolated directly from the relevant cells or it may be produced by in vitro priming from a suitable RNA promoter or by in vitro transcription.

The present invention may be used for the detection of variation in genomic DNA whether human, animal or other. It finds particular use in the analysis of inherited or acquired diseases or disorders. A particular use is in the detection of inherited disease. It will be appreciated that the target nucleic acid is directly or indirectly linked to the sequence or region of interest for analysis. In one preferred aspect the primer of the invention is used as the common primer in a PCR in combination with an ARMS primer (as disclosed in for example EP-B1-0 332 435). This is an example of indirect linkage to the sequence or region of interest. Alternatively the sequence or region of interest is identified when it interacts with the template specific region in an allele specific manner, preferably as an ARMS primer (see above). Alternatively, the sequence or region of interest may be identified by allele specific interaction with the target binding region in the primer tail. Still further, the sequence or region of interest may be a combination of the target region and template binding seqence in the primer provided that hybridisation of the target binding region in the primer tail is dependent on formation of a primer extension product.

In addition to the gene based diagnostics of human heritable disease, the invention will be useful in the detection of amplicons from other sources. A particular use is in the detection of infectious agents (bacteria, viruses etc), such as HIV, where the combination of allele specific priming and allelic discrimination via the target binding region offers opportunities to monitor the emergence of particular variants of HIV within a virus population in a patient. Other infectious agents for which quantitative data (measured by Real time PCR) would be helpful include Hepatitis C virus and others.

In other medical microbiology applications it is important to be able to detect and quantify particular species of micro-organism. The use of fluorescent Scorpions primers greatly facilitates this.

The presence of bacteria in food or other products can also be usefully monitored using real time PCR with Scorpions fluorescence methods. The specificity of probe detection can be modified to permit or exclude the detection of related targets.

A particular advantage is that the novel primers of the invention need not be used at 100% primer concentration, that is to say the detection method works well even where only a small proportion of novel to conventional primer is used. Whilst we do not wish to be bound by theoretical considerations we believe that as little as a few percent, say up to 10%, up to 20%, such as up to 30%, up to 40% or up to 50% or 60% novel primer is used. Alternatively at least 50%, 60%, 70%, 80%, 90% or 100% novel primer is used.

The primer(s) can be added at any convenient stage in an amplification reaction, for example in the final amplification cycle, all that is required is one or more primer extension reactions. For homogeneous detection systems it is preferable to add the primer(s) at the start of any amplification procedure.

The primer tail may be configured in a number of different ways, the sole requirement is that the target binding region in the tail is available after primer extension to hybridise with a complementary sequence (if present) in the primer extension product. In its simplest form the primer tail is randomly coiled, if fluorescent detection means are used the primer is self-quenched prior to hybridisation of the target binding region.

The primer may include one or more regions of internal hybridisation which help stabilise the signalling system in a given position i.e. a particular configuration. Such region(s) are conveniently located within the primer tail and may each be of 2 or more base pairs. The configurations adopted are limited only by practical considerations and may include the use of one or more structures selected from hairpins, arms, elbows, stems, bubbles and loops. Once convenient structures have been devised these may be used as common features in the tailed primers of the invention.

The target binding region may have any convenient number of additional bases at its 5' end. All or some of these additional bases may form part of any region(s) of internal hybridisation.

In a further aspect of the invention the primer may comprise a capture region. This may be placed at any convenient location, preferably on the primer tail. The capture region may be a contiguous or branched structure (cf. FIG. 8c) The capture region hybridises to complementary sequence on, for example a solid phase.

Any convenient template dependent polymerase may be used, this is preferably a thermostable polymerase enzyme such as taq, more preferably taq Gold.

Similarly any convenient nucleoside triphosphates for conventional base pairing may be used. If required these may be modified for fluorescence. As these may affect polymerisation rates up to only about 1 in 20 dNTPs used is modified for best results.

Further details of convenient polymerases, nucleoside triphosphates, other PCR reagents, primer design, instruments and consumables are given in "PCR" by C. R. Newton and A. Graham (The Introduction to Biotechniques series, Second Edition 1997, ISBN 1 85996 011 1, Bios Scientific Publishers Limited, Oxford). Further guidance may be found in "Laboratory protocols for mutation detection" edited by Ulf Landegren, published by the Oxford University Press, Oxford, 1996, ISBN 0 19 857795 8.

The invention will now be further illustrated by the following non-limiting specific description wherein the tailed primers of the invention are referred to as Scorpions primers:

The design of Scorpions primers may follow well known guidelines for PCR amplimers; the 3' end of the Scorpions primer and/or the target binding region may taken directly from, for example an existing PCR or ARMS assay.

Target binding regions are typically about 17 bases (DNA) although (depending upon the temperature at which measurements are to be taken) shorter (as little as 6 to 10 bases) target binding regions be used. In this context we envisage that non-natural nucleic acids such as PNA or 2'-O-alkyl-RNA (particularly 2'-O-methyl RNA) will be useful since they have higher $T_m$s when bound to their targets. The spacing on a DNA strand between the amplicon binding region and its complementary sequence within the amplicon may be as little as 30 bases (that is directly abutting the primer region) or may be as much as about 200–300 bases. The efficiency of the unimolecular interaction is expected to decline as this distance increases.

Where stem regions are used, they may range from 2 bases (especially useful for 2'-O-methyl RNA or PNA) to about 6, 8, 10 or more bases. The balance between stem length and amplicon binding length is important: the probe-target complex should have a stronger (more negative) $\Delta G$ (free energy) than the stem duplex at the assay temperature. Any polymerisation blocking group such as those described in our EP-B1-0 416817 (Zeneca Limited) is suitable. However, we prefer that it should be easily incorporated by solid phase oligonucleotide chemistry and should also form a substrate for further extension in the same chemistry. Convenient examples include hexethylene glycol (HEG) and tetraethylene glycol (TEG) phosphoramidites.

The range of assays which can be performed using the Scorpions primers is extensive. Detection may, for example, be effected after PCR amplification and at room temperatures since the unimolecular hybridisation events happen quickly and are stable for extended periods (at least overnight). Furthermore, positive fluorescence signals are so high and backgrounds so low, that fluorescence can be observed by eye under appropriate illumination and at ambient temperature. These are significant advantages.

Where allelic discrimination is employed as an endpoint, this may require the use of temperature control to selectively destabilise mismatched target.

The Scorpions primers of this invention are particularly suited to real time assays since signal generation is rapid and requires only a unimolecular interaction. Additionally, backgrounds are low and signals are high allowing a good deal of flexibility in assay design. Continuous monitoring of fluorescence through the PCR is possible with the appropriate hardware.

Scorpions primers also have substantial benefits for in situ techniques such as in situ PCR (ISPCR) and primed in situ synthesis (PRINS). Only priming events which generate the desired product produce signal and this provides substantial benefits over other techniques for detecting products within a cell.

It is generally desirable to include the Scorpions primer at the beginning of the reaction and to measure fluorescence in the closed tube (homogeneous) either continuously or post-PCR. Alternatively the Scorpions primer may be added at a later stage of the amplification; the only requirement is that the Scorpions primer must undergo a single round of extension and produce the unimolecular tail/target duplex.

Using appropriate signalling systems (for example different fluorophores) it is possible to combine (multiplex) the output of several Scorpions primers in a single reaction. The number of primers that may be used is limited only by experimental considerations.

We now disclose the following non-limiting embodiments:

Fluorphore/Quencher Embodiment

See FIG. 1. Quenching is achieved by the random folding of the tail bringing the fluorophore/quencher (F/Q) pair into proximity by chance (FIG. 2). In order to maximise this quenching, it is preferred but not essential to have the fluorophore in the middle of the molecule with the quencher at the 5' end. Signal "switch-on" is by the same loss of quenching caused by hybridisation of the probe (FIG. 3). In this embodiment, it is not critical that the F and the Q are at opposite ends of the probing entity, and it may be beneficial to place them closer together within the probe portion. It is important, though, not to disrupt the target binding fimction of the tail by introducing bulky, non base-pairing elements, but both fluorophore and quencher could be introduced on uracil monomers, replacing thymidines in the probe. We believe that this embodiment may work best as an amplicon detector.

Intercalation Embodiment

In this embodiment, the design of the Scorpions primer is further simplified, having no quencher involved. Instead, the tail carries an intercalating dye which is capable of being incorporated between the bases of a double stranded nucleic acid molecule, upon which it becomes highly fluorescent. In this way, sequence specific intercalation is achieved (FIGS. 4a,b). In contrast to the "no-stem" method described in the previous embodiment, the intercalating fluorophore is better placed at the 5'-terminus of the Scorpions molecule or as an internal part of the loop. Internal folding within the primer is best minimised to ensure the absence of double stranded DNA which may then be intercalated, leading to high background noise. If the dye is placed within the loop portion of the molecule, it may be possible to have a hairpin structure (which would enhance the allele specificity of the the hybridisation). The dye used is preferably not a standard fluorophores but rather an intercalator having low fluorescence in the absence of double stranded target and a high enhancement when intercalated. Suitable fluorophores include the cyanine dyes developed by Molecular Probes, ethidium bromide, acridine and others. The dyes may need to be modified to ensure their easy attachment to the Scorpions primer or incorporation via phosphoramidite (solid phase) chemistry.

FRET Embodiment

In this modification of the basic system, the dyes involved form an energy transfer pair. One of the dyes is positioned close to the 3' end of the target binding region, while the other is placed close to the 3' terminus of the amplicon binding region (see FIGS. 5a,b). The probe must hybridise very close to the primer thus bringing together the FRET pair and producing an enhanced fluorescence signal No-quencher Embodiment A fluorophore is attached to the tail of the Scorpions primer (see FIGS. 6(a),(b) & (c)). Random folding of the Scorpions primer around the fluorophore provides sufficient quenching of the fluorophore. We believe this may be due principally to the nucleotide, guanylic acid. In order to maximise quenching it is preferred, but not essential, to have the fluorophore at or around the middle of the primer, with sufficient additional DNA to quench efficiently. Quenching efficiency is dependent on the sequence of the surrounding DNA. Binding of the target binding region of the tail to the target region alters the conformation of the DNA sufficiently to remove this quenching. We prefer this embodiment as an amplicon detector.

Bimolecular Embodiment

The fluorophore and quencher may be introduced on two separate but complementary molecules (FIG. 7a). The fluorophore and quencher may be on either end of the probe or complementary strands, provided that hybridisation of the two strands brings the fluorophore/quencher pair into close proximity. After a round of denaturation, annealing and extension, the fluorophore remains quenched, as the bimolecular moiety re-forms (FIG. 7b). The non Scorpion, free strand is in excess to ensure that this bimolecular interaction occurs and for this reason it is preferred that this molecule carries the quencher, to minimise backgrounds. However, after a further round of denaturation and annealing, the self-probing strand forms (FIG. 7c) and the free quencher (oligo) is unable to compete with this event kinetically or thermodynamically thus leading to an increase in fluorescence.

If required one of the molecules may comprise a secondary structure such as a hairpin structure so as to allow the attachment of for example more quencher species for more efficient quenching of a fluorophore on the other molecule.

Capture Probe Embodiment

In addition to the embodiments discussed above, amplicons may be specifically captured and probed using the same non-amplifiable tail (see FIGS. 8a & 8b). In a further specific embodiment the capture and tail sequences are provided as non-contiguous features ie. together with the template binding region they form a branched primer structure (cf, FIG. 8c). After amplification the amplicon may be captured onto a solid surface, whilst the signal generation remains amplicon specific. Alternatively the capture sequences and signalling system may be on opposite ends of the amplicons. In this way, generic "chips" with the same capture sequences may be used to analyse many different targets—the capture regions remain unchanged while the amplifier and probe elements vary.

Stem Embodiment

In this embodiment the primer tail comprises self complementary stems (also DNA, RNA, 2'-O-methyl RNA, PNA and their variants) which flank the amplicon binding region and which carry a fluorophore quencher pair, such that hairpin formation by the two stems brings the F/Q pair together causing the fluorescence to be substantially quenched ("off"). The fluorophore and quencher can be placed on either arm, depending upon preference or synthetic simplicity; we prefer to have the quencher on the 3' arm (ie adjacent to the blocker in the middle of the molecule)]. At high temperatures, the stem duplex is disrupted and the fluorophore is unquenched (ie "on"—FIG. 9a); at lower temperatures, however, the stem duplex forms and the fluorescence is substantially off (FIG. 9b).

In an Amplification Cycle

After initial denaturation, annealing and extension, the Scorpions amplicon comprises a region complementary to the loop region at its 5'-end (FIG. 10a). Upon a second round of denaturation (FIG. 10b) and annealing, the tail hybridises to the newly synthesised region with great efficiency (a unimolecular interaction) and fluorescence remains unquenched (FIG. 10c). Unextended primers, however, will continue to form their quenched conformation. Meanwhile, the "reverse" primer will have hybridised to this same strand and synthesis goes on. We believe that the tail is (at least partially) displaced by the Taq polymerase and the remainder melts off easily since the probes are short. At this stage, the Taq polymerase completes the synthesis of this strand until it encounters the amplification blocker. Because signals are strong and the priming function is identical to the non-Scorpions variant, not all the primer needs to be in the Scorpions form. Indeed, we have obtained strong signals when 10% or less of the primer was in the Scorpions form. This allows cheaper reactions and also permits the balancing of signal strengths where two different fluorophores are used.

The Scorpions primers of the invention may be used in place of conventional amplification primers, such as PCR primers and are not expected to interfere with their amplification function. In a two-tube ARMS test (normal and mutant) the Scorpions primer may conveniently be the common primer (FIG. 11a), with the production of signal dependent upon ARMS amplification.

However, it is equally viable to place the signalling entity on the ARMS primers. Each ARMS primer may be labelled with different fluorochromes (F1, F2), thus permitting single tube genotyping (STG)—that is both reactions are run in the same tube and the amplicons are distinguished by their characteristic "colour" (FIG. 11b). Alternatively, the signalling entity may carry the allelic specificity (see Example 2): the primers are standard (non-ARMS) primers and two different probe sequences to match the two allelic variants are introduced on two variants of one of the primers (FIGS. 12a,b). It has been found that probes which can form hairpins in the absence of target are better discriminators of single base mismatches than the untailed versions of the same probes. In another manifestation, probes for each variant may be introduced one each on the two amplimers (FIGS. 12c, d) thereby probing different strands of the reaction. Finally, combinations of these ideas are possible: one subset of Scorpions primers may be used for allele discrimination, while other primers in the same mix may act as control probes to detect the amplicon itself (FIG. 12e). Discrimination between these events is achieved either by fluorescence wavelength or alternatively by the use of probe elements having the same fluorophore but different $T_m$s which may then be discerned by measuring the fluorescence over a temperature range.

The invention will now be illustrated but not limited by reference to the following Figures and Examples wherein.

Figure 1:
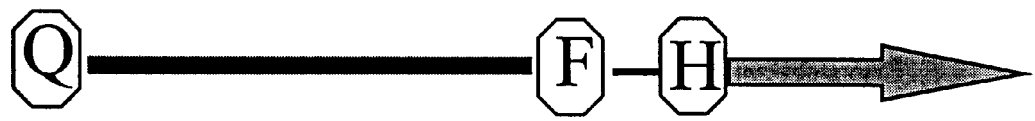
FIG. 1 shows the basic features of a convenient primer design, the template binding region is indicated by the shaded arrow, the tail region comprises a blocking group indicated by H, also shown are a quencher and fluorophore, the target binding region is in the region indicated by the solid line between the quencher and fluorophore.
Figure 2:
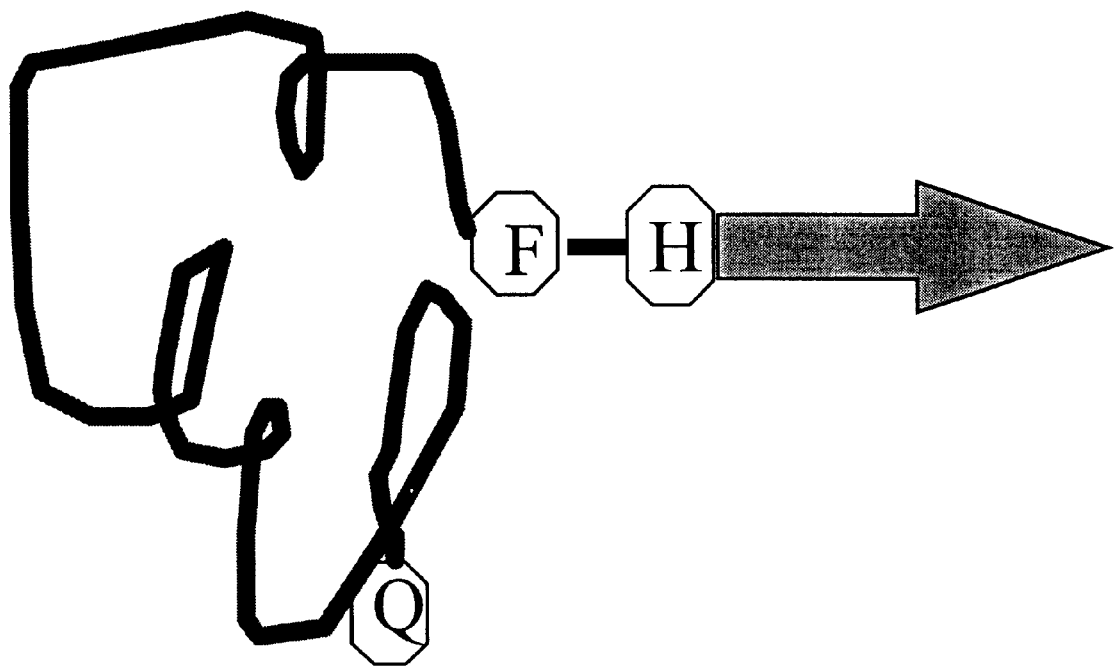
FIG. 2 shows quenching achieved by random coiling of the tail bringing the fluorophore and quencher pair into close proximity.
Figure 3:
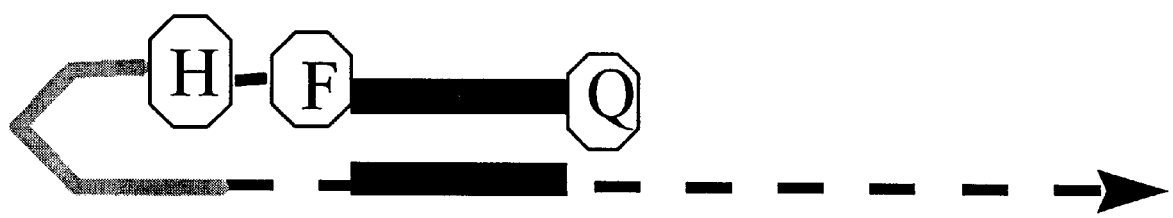
FIG. 3 shows hybridisation of the target binding region to a complementary sequence in the primer extension product corresponding to the target region.
Figure 4:
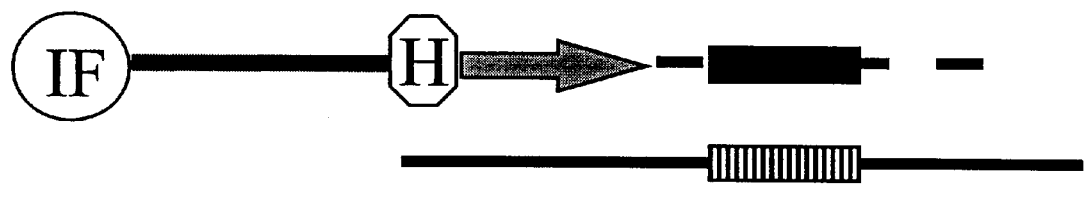
FIG. 4(a) shows the inclusion of an intercalating fluorophore (IF) in the tail of the primer and primer extension on a sample template, (b) shows intercalation after hybridisation of the target binding region to a complementary sequence in the primer extension product corresponding to the target region.
Figure 4:
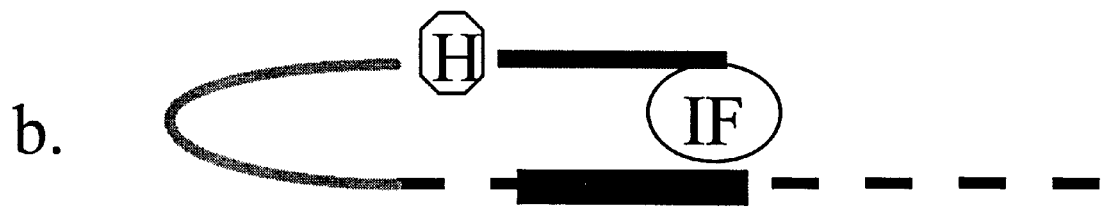
Figure 5:
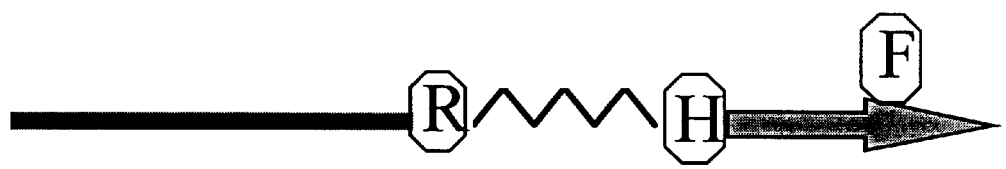
FIG. 5(a) shows the use of dyes (R & F) incorporated into the primer and which form an energy tranfer pair, (b) shows their relative position upon hybridisation.
Figure 5:
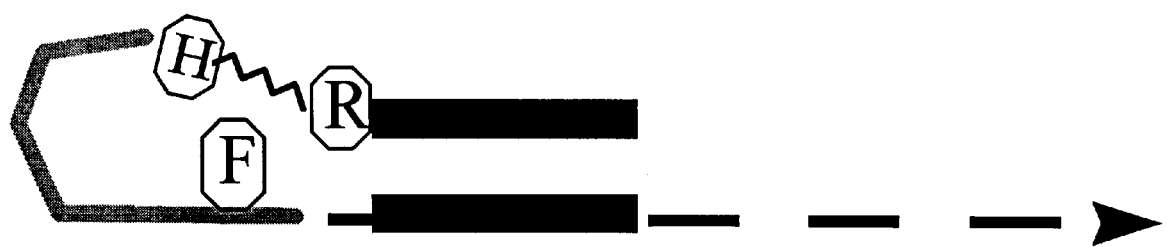
Figure 6:
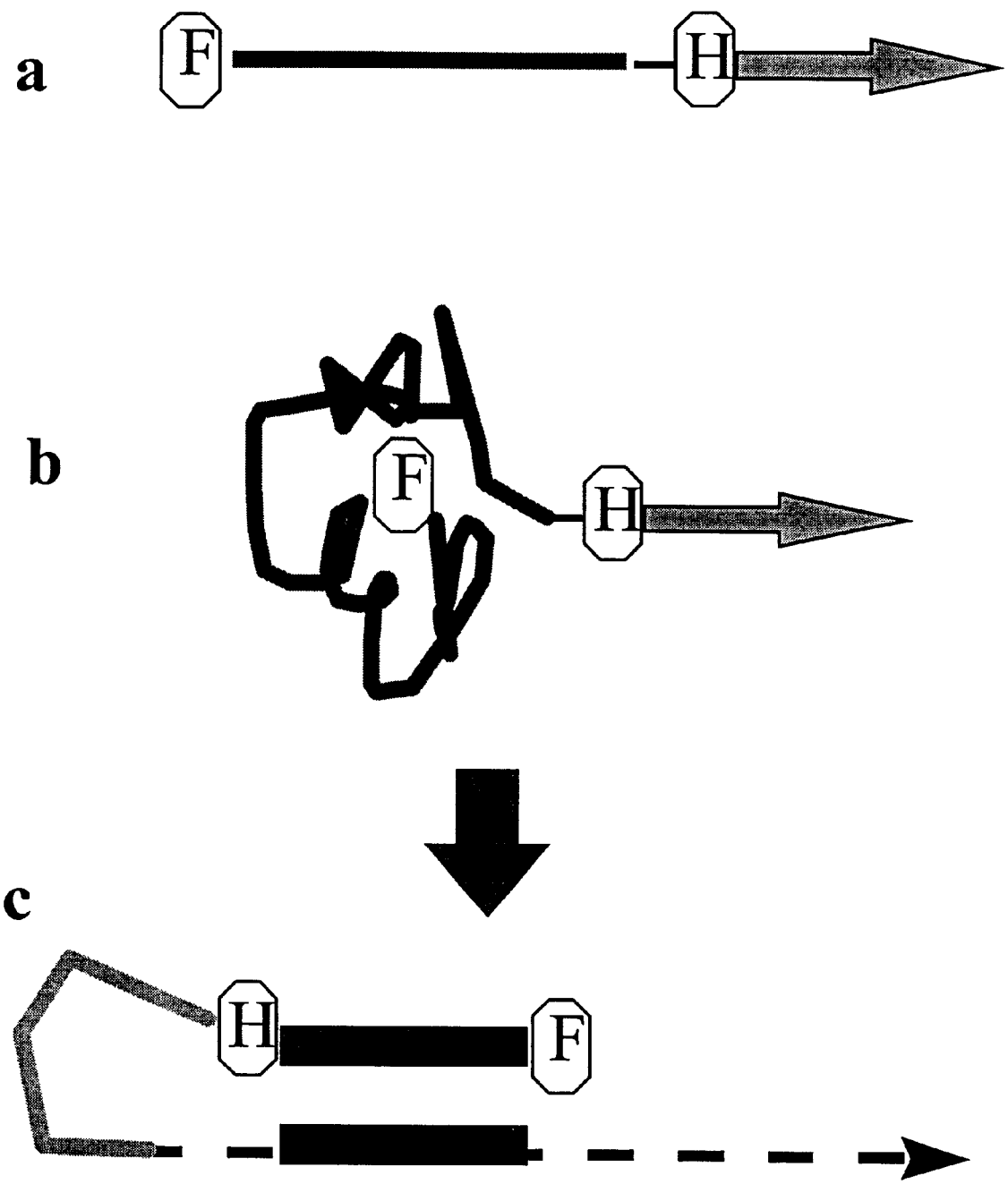
FIG. 6(a) shows the use of a primer having a single fluorophore (F) attached at the 5' terminus, a blocking group (H) is shown, the target binding region is indicated by the arrow to the right, (b) shows the random coiling and quenching of the fluorophore in solution and (c) shows hybridisation of the target binding region after primer extension.
Figure 7A:
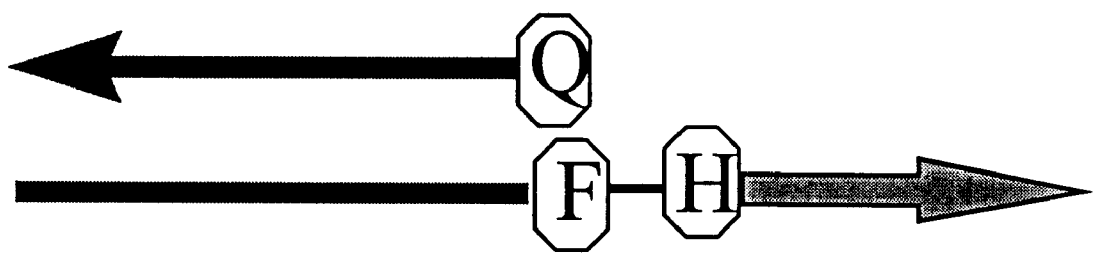
FIG. 7(a) shows the bimolecular embodiment of the invention, the fluorophore and quencher are provided on separate species, in (b) the primer is extended on a sample template, and in (c) separation of the fluorophore and quencher upon hybridisation of the target binding region are shown.
Figure 7B:
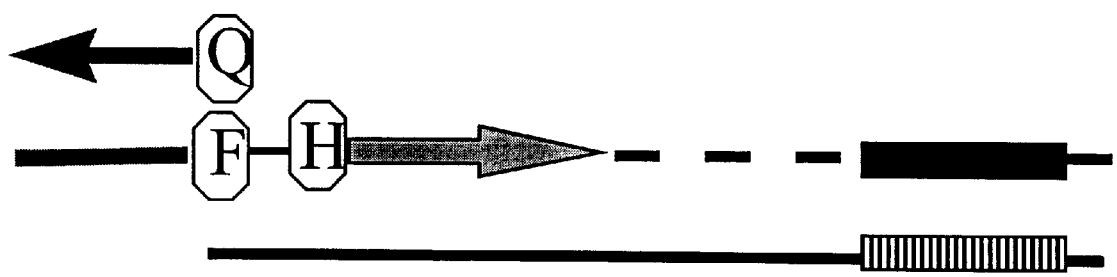
Figure 7C:
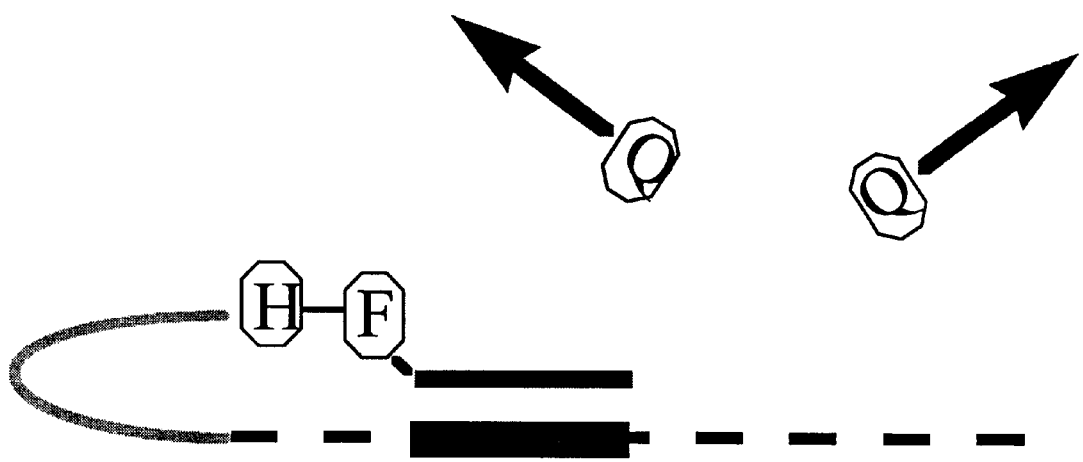
Figure 8A:
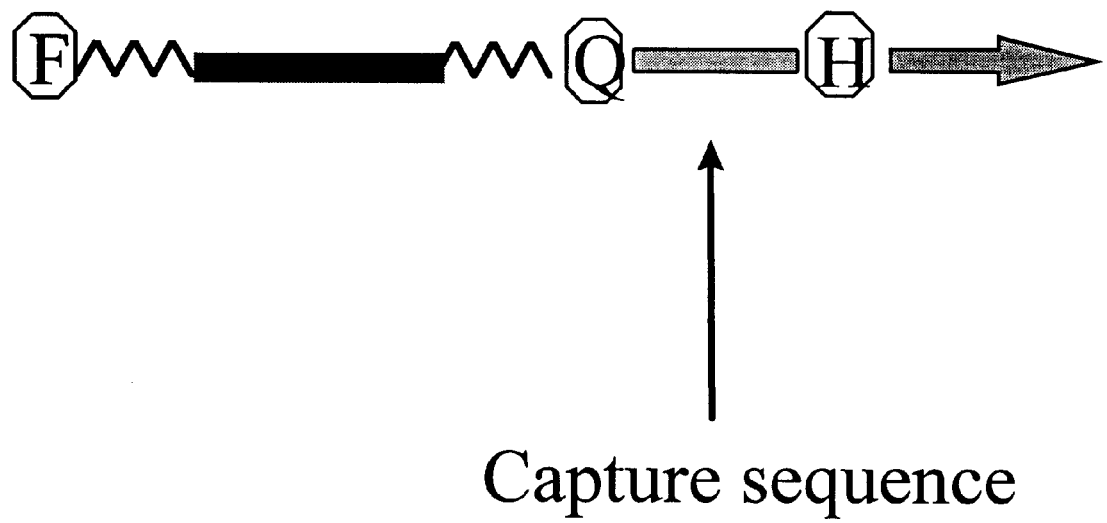
FIG. 8(a) shows the capture probe embodiment of the invention, in (b) amplicons are captured on a solid phase and probed using the same non-amplifiable tail, in (c) the primer comprises a branched structure of the tail and capture sequences.
Figure 8B:
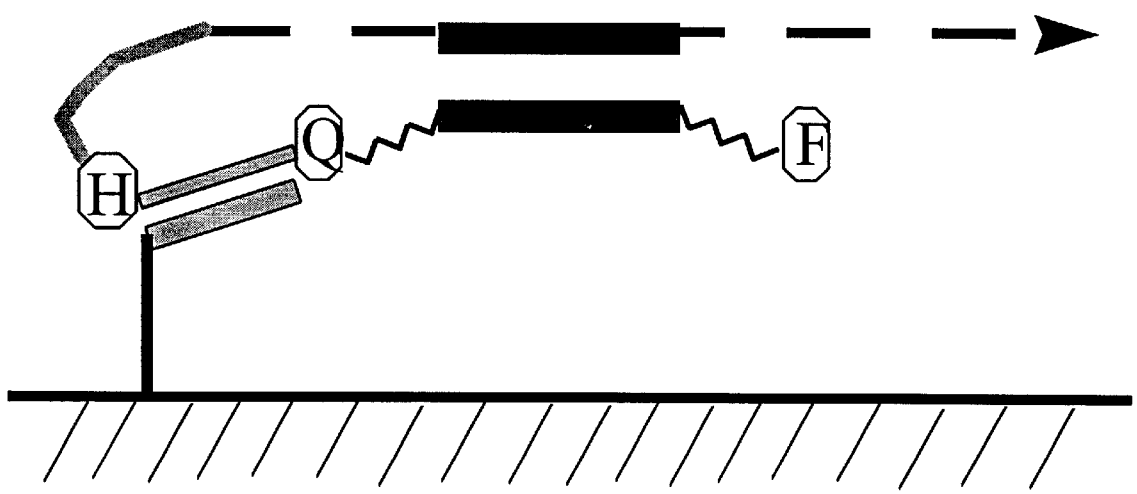
Figure 8C:
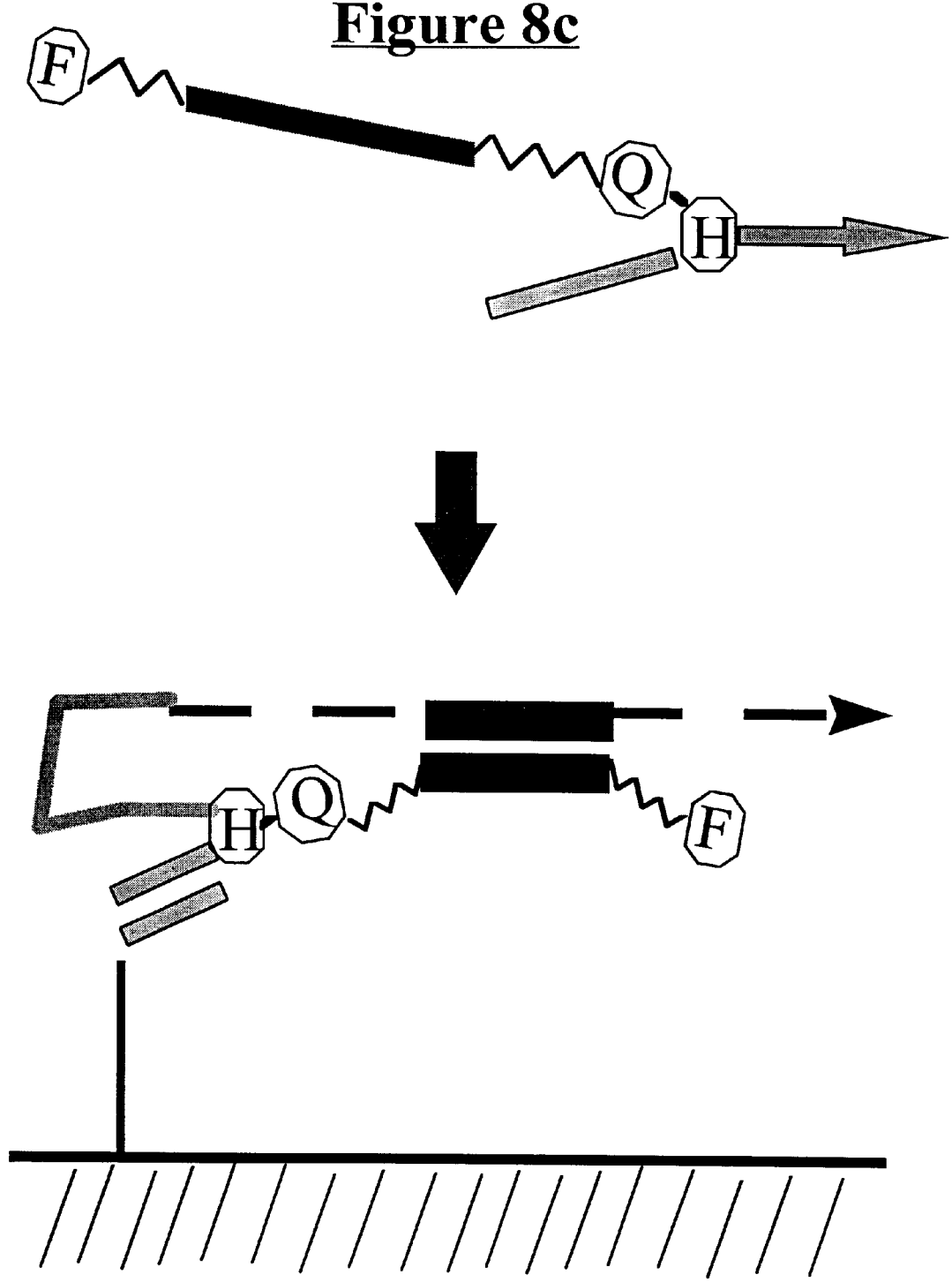
Figure 9:
FIG. 9 shows the stem embodiment of the invention, (a) at high temperatures, the stem duplex is disrupted and the fluorophore is unquenched, ie. "on"; (b) at lower temperatures, however, the stem duplex forms and the fluorescence is substantially off.
Figure 9:
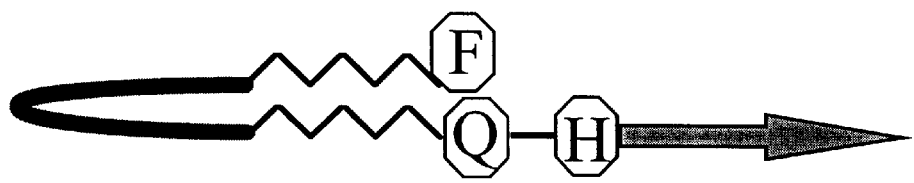
Figure 10A:
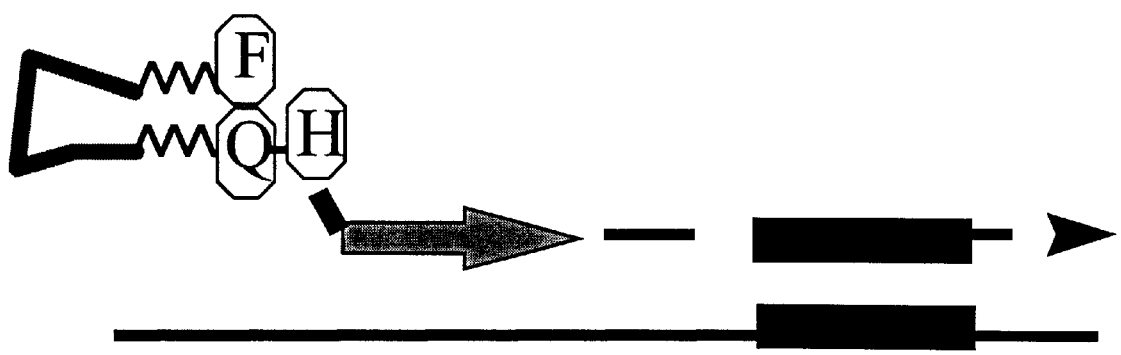
Figure 10B:
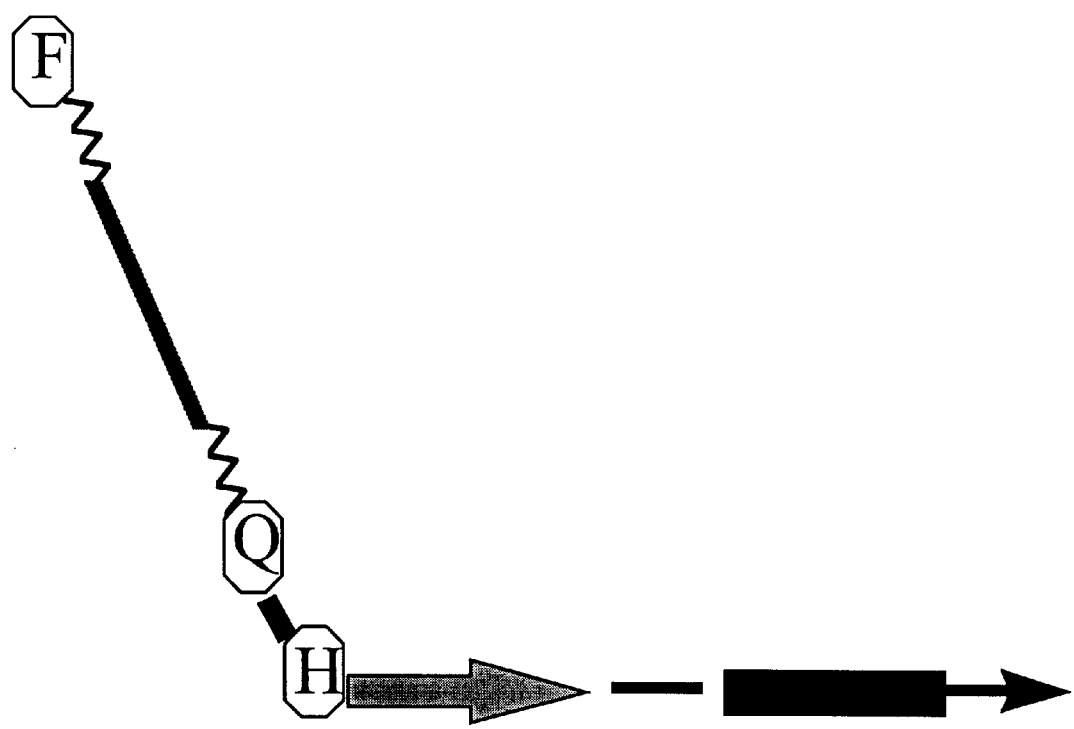
Figure 10C:
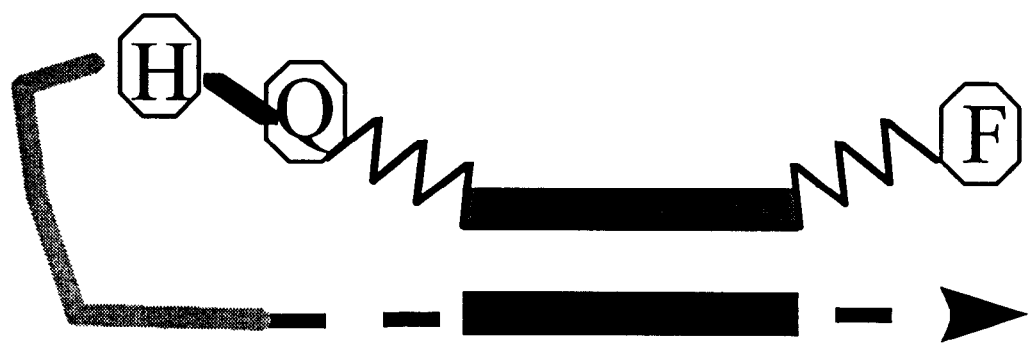

FIG. 10 shows the primer as used in an amplification cycle. (a) after initial denaturation, annealing and extension, the Scorpions amplicon comprises a region complementary to the loop region at its 5'-end; (b) upon a second round of denaturation and annealing, the tail hybridises (c) to the newly synthesised region with great efficiency (a unimolecular interaction) and fluorescence remains unquenched (FIG. 10c). Unextended primers, however, will continue to form their quenched conformation.

Figure 11A:
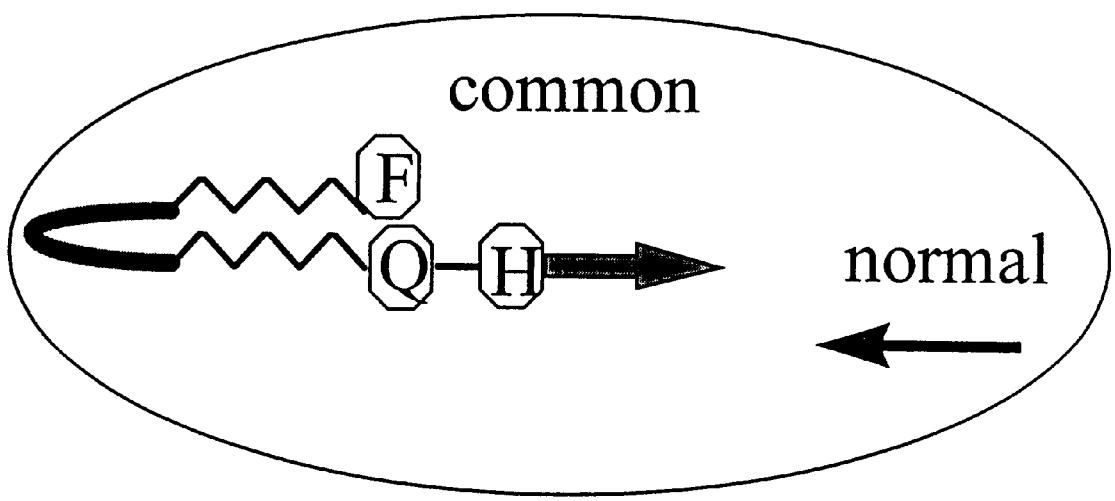
Figure 11A:
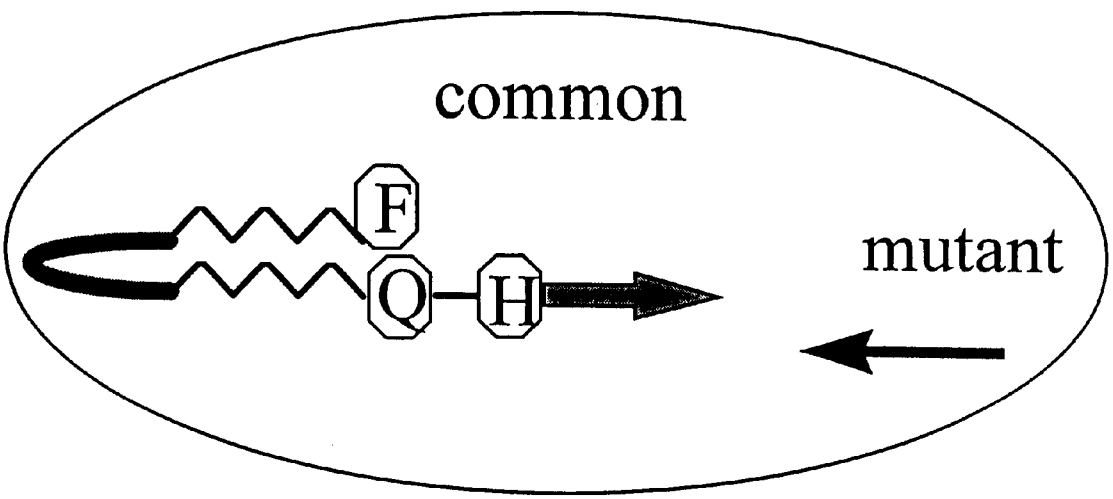
Figure 11B:
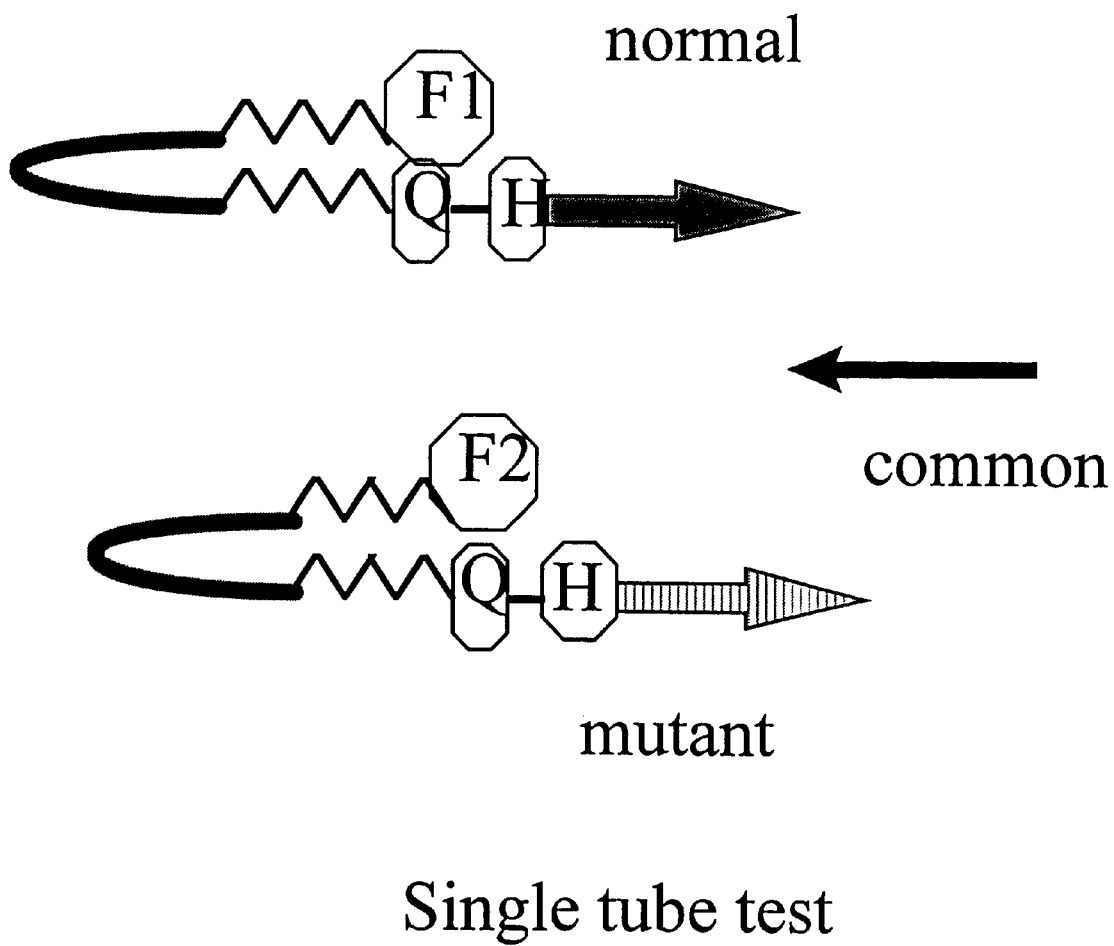
Figure 12A:
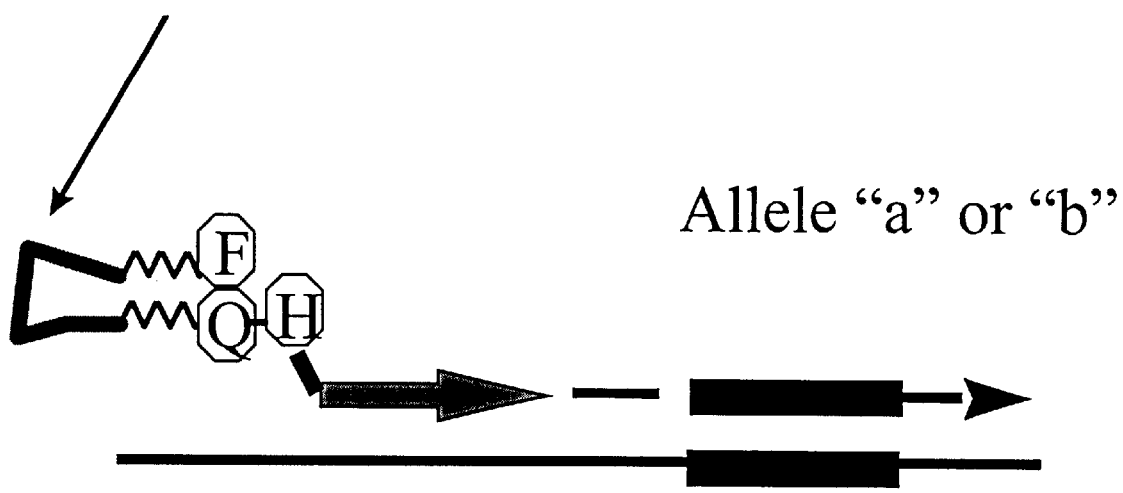
Figure 12B:
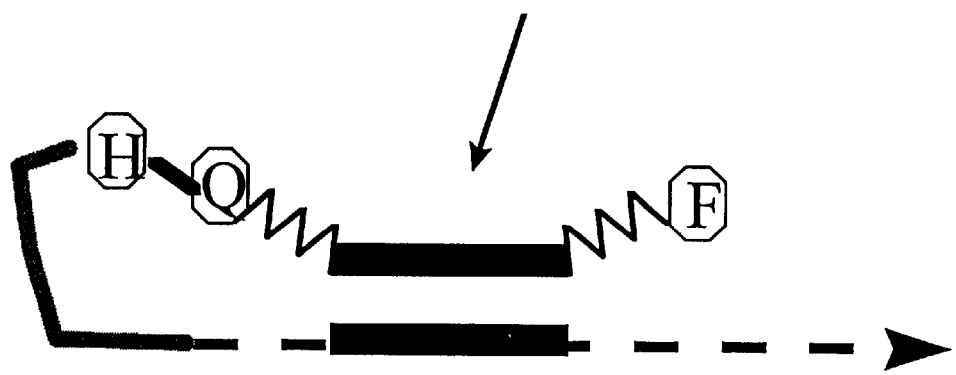
Figure 12B:
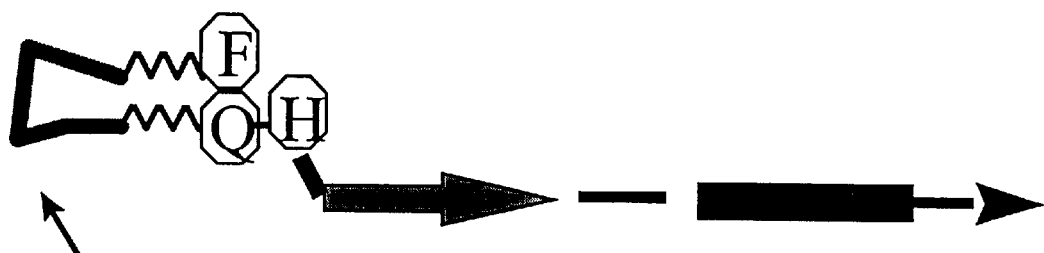
Figure 12C:
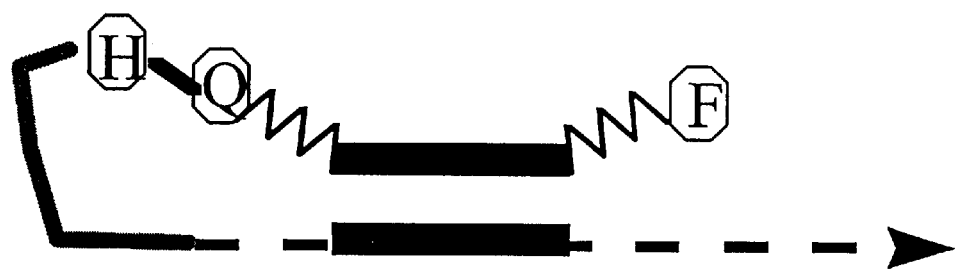
Figure 12C:
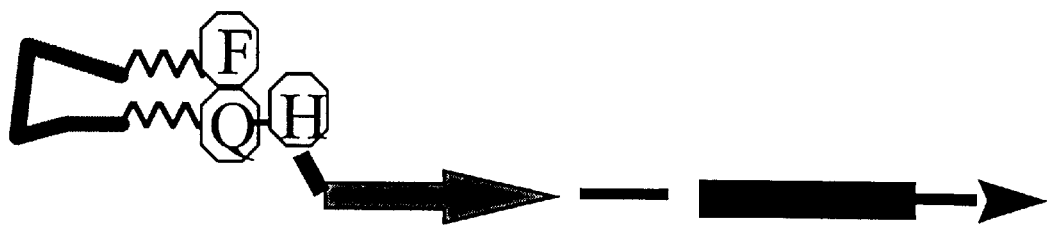
Figure 12D:
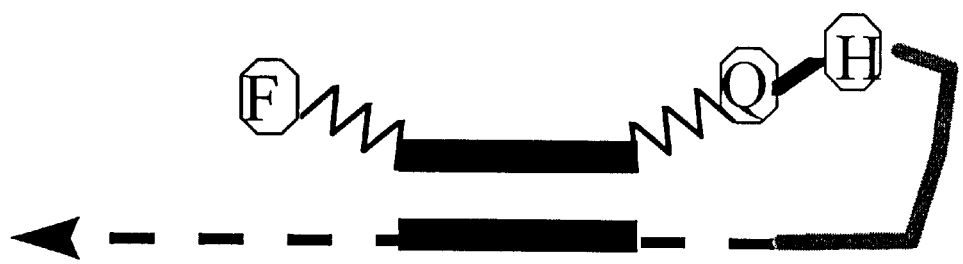
Figure 12D:
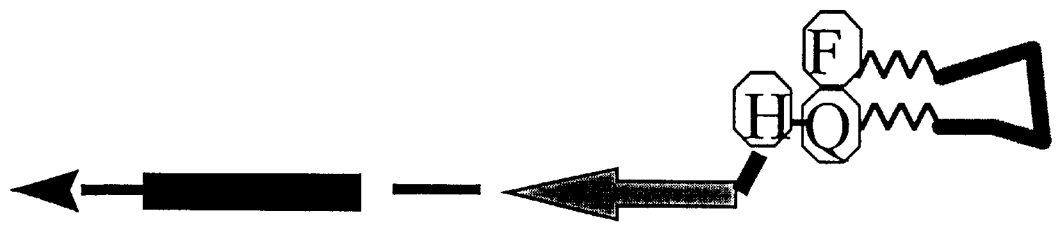
Figure 12E:
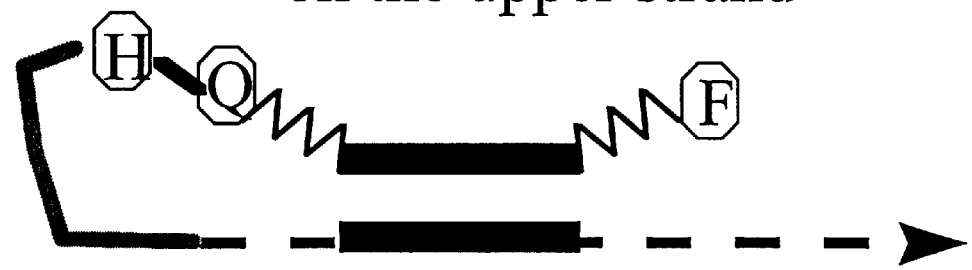
Figure 12E:
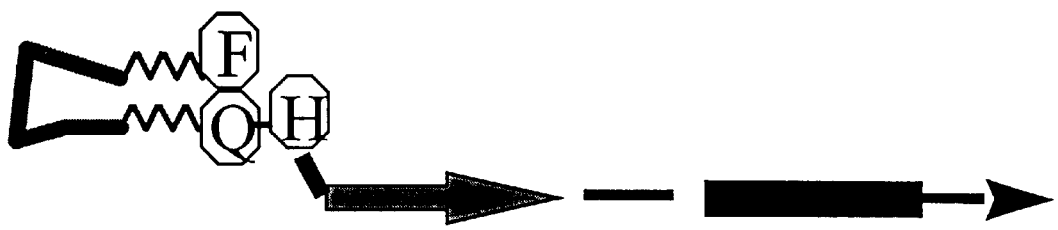
Figure 12E:
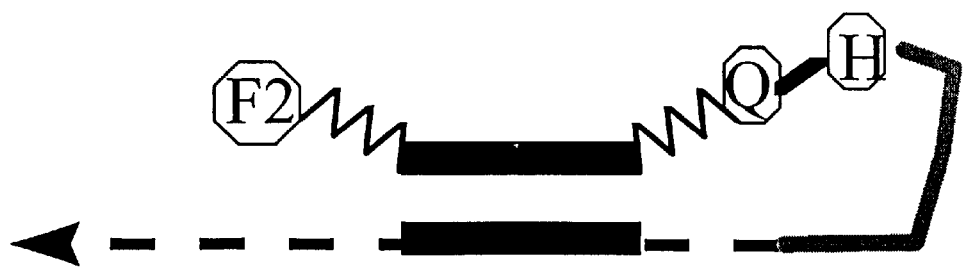

FIG. 11 shows use of the primer as (a) a common primer in a two tube ARMS test and (b) as allele specific primers "a" and "b" in a single tube ARMS test.

FIG. 12 shows the use of the primer where hybridisation of the target binding region occurs in an allele specific manner, in (a) primer extension gives a product corresponding to allele "a" or "b", in (b) hybridisation is allele specific or mismatched in (c) and (d) probes for each variant are provided on each of the two amplimers, thereby probing different strands of the reaction, and in (e) different primers may be used in the same mix for allele discrimination and as control primers for amplicon detection.

Figure 13:
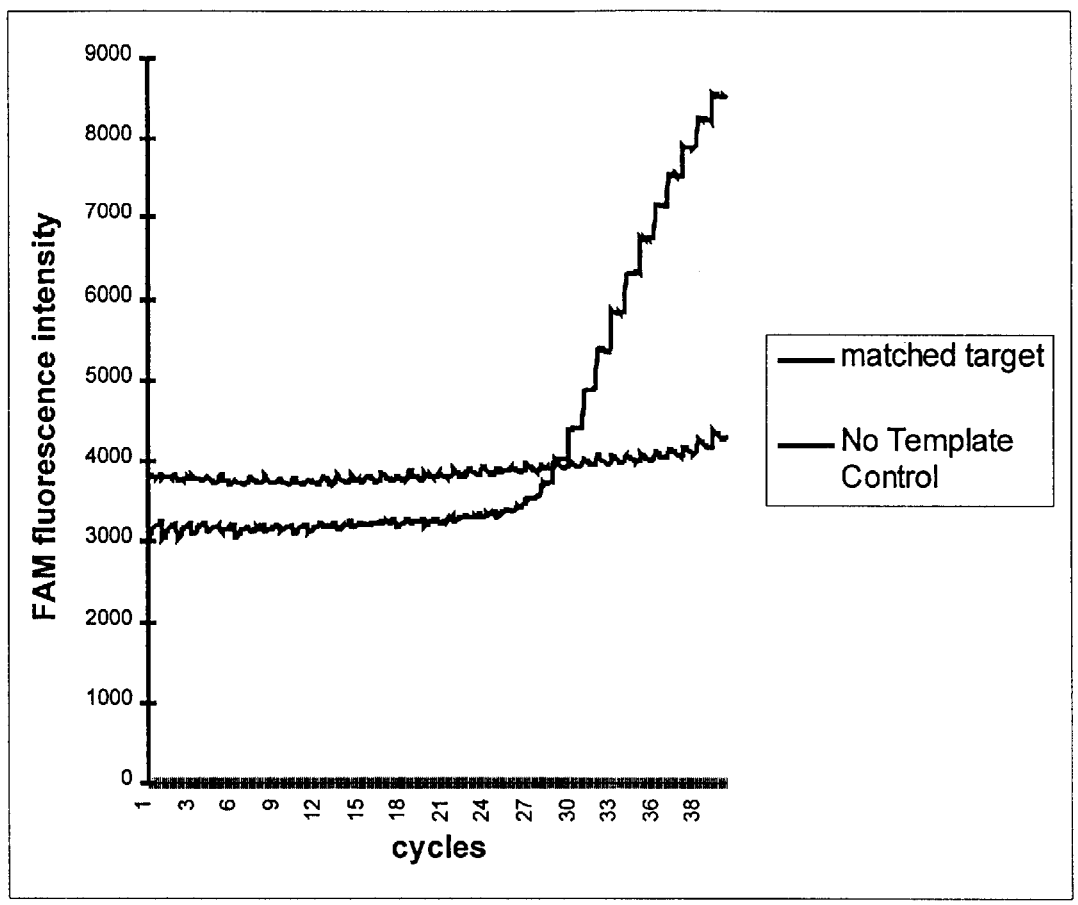

FIG. 13 shows real time detection of amplification, fluorescent signal is generated upon hybridisation of a matched target binding region in contrast to a mismatched target.

Figure 14:
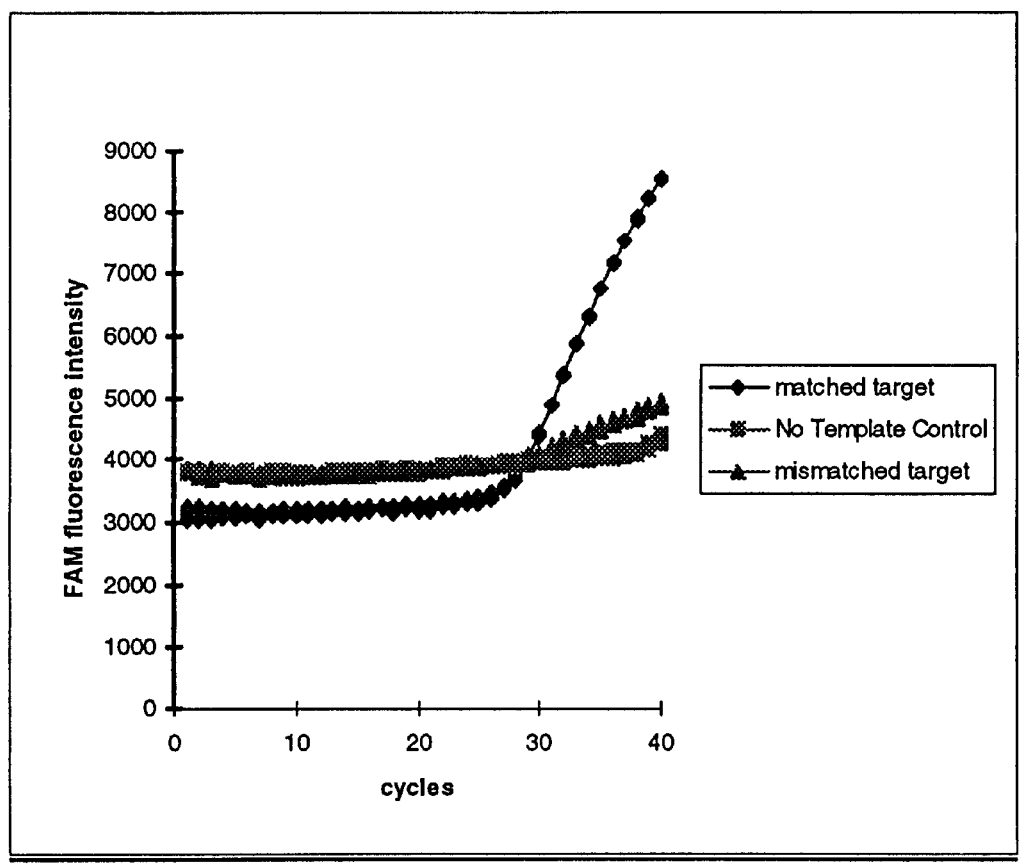
Figure 15A:
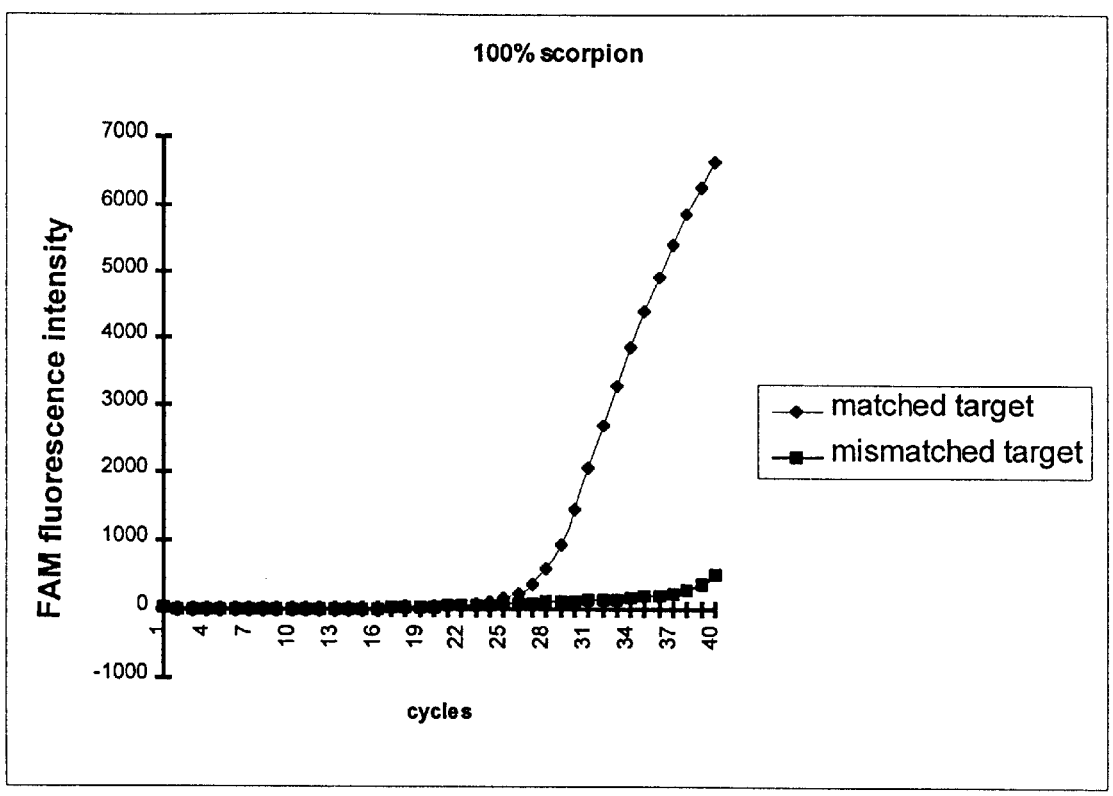
Figure 15B:
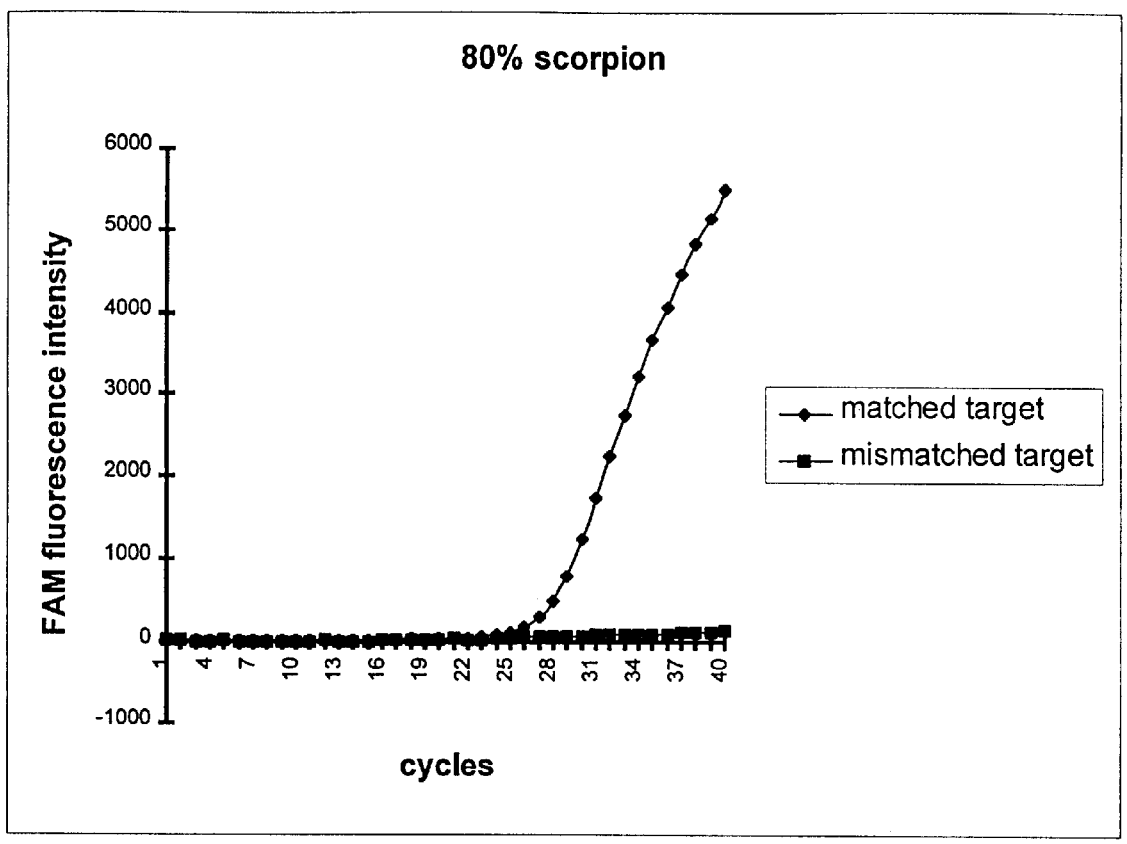
Figure 15C:
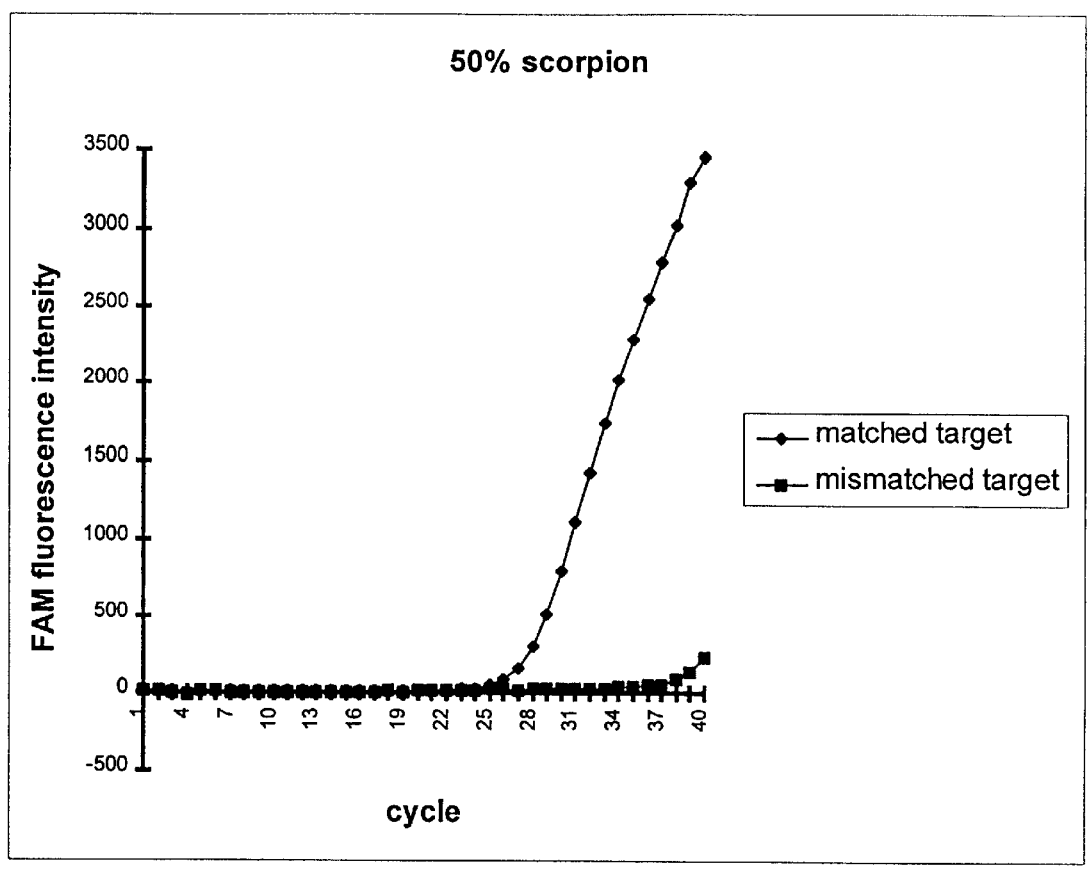
Figure 15D:
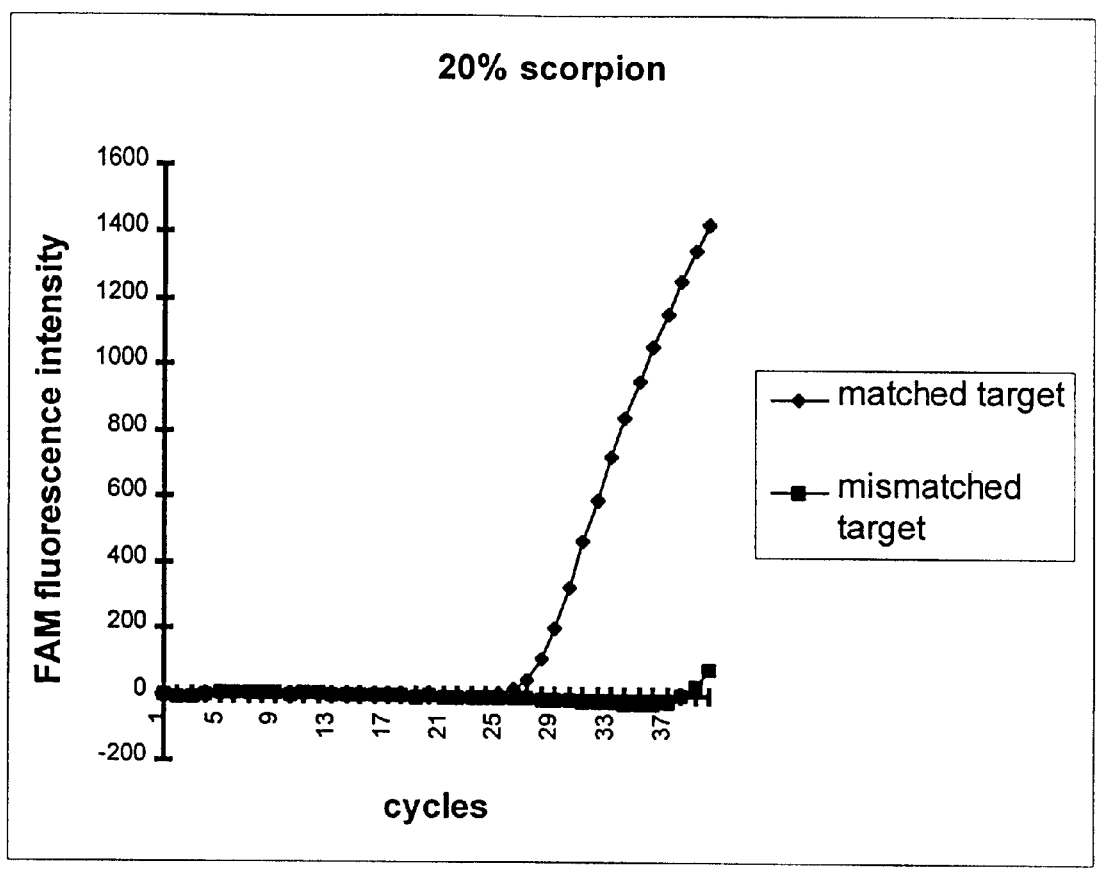
Figure 15E:
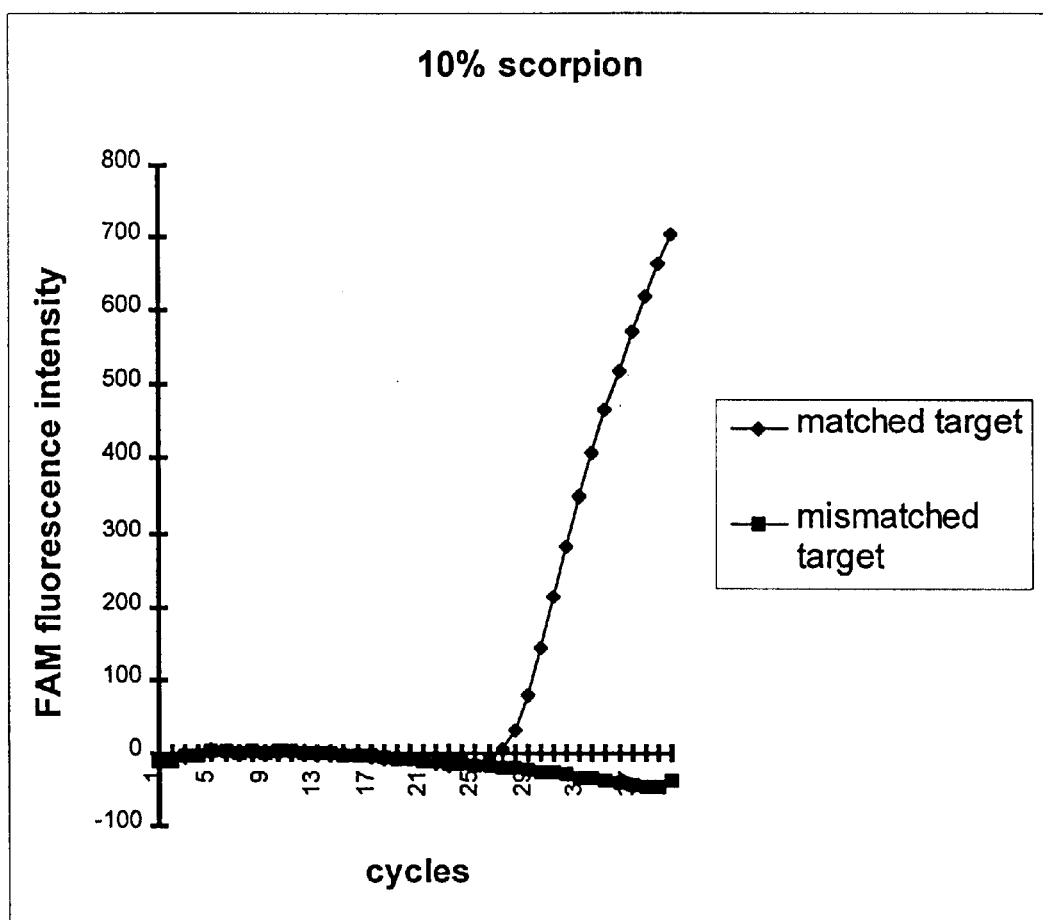

FIG. 14 shows allele discrimination, fluorescent signal is generated upon hybridisation of a matched target binding region in contrast to a no-template control and a mismatched target.

FIG. 15 shows primer titration, fluorescent signal is generated upon hybridisation of a matched target binding region in contrast to a mismatched target. The following proportions of Scorpion primer were used: (a) 100%, (b) 80%, (c) 50%, (d) 20% and (e) 10%.

Figure 16:
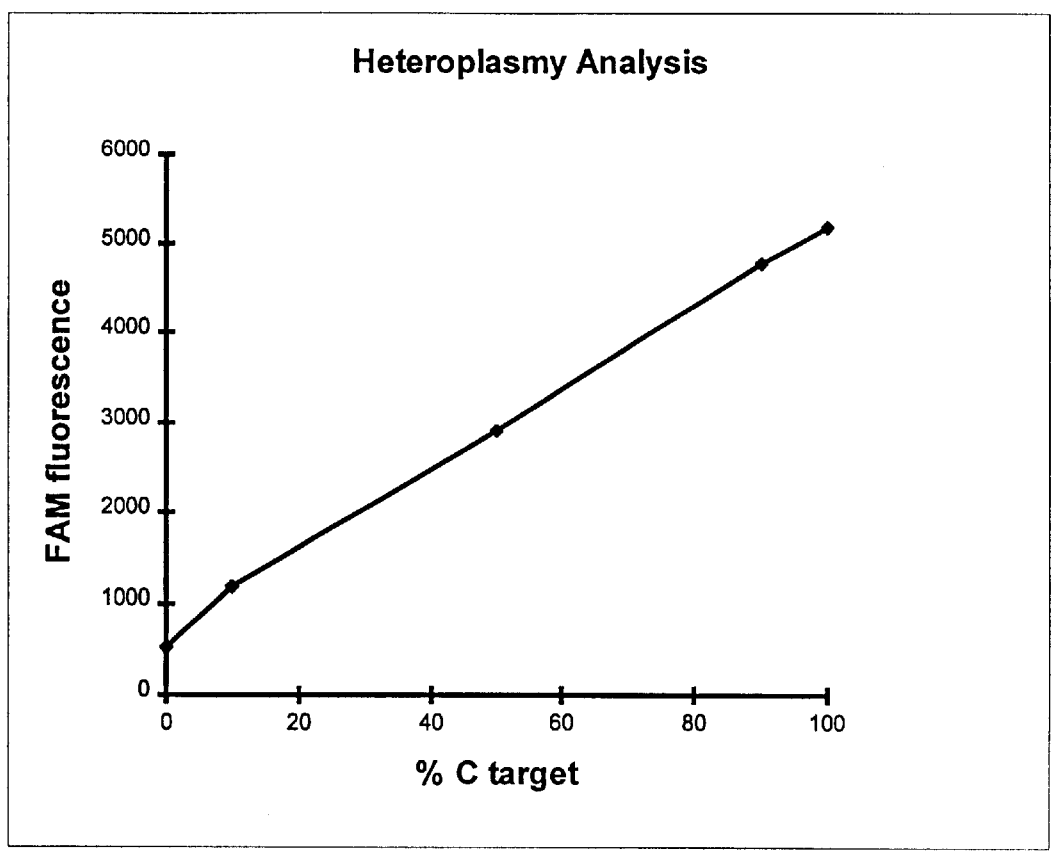

FIG. 16 shows heteroplasmy analysis, varying admixtures of C homozygote and A homozygote were used as shown and readings taken after 40 cycles of PCR.

Figure 17A:
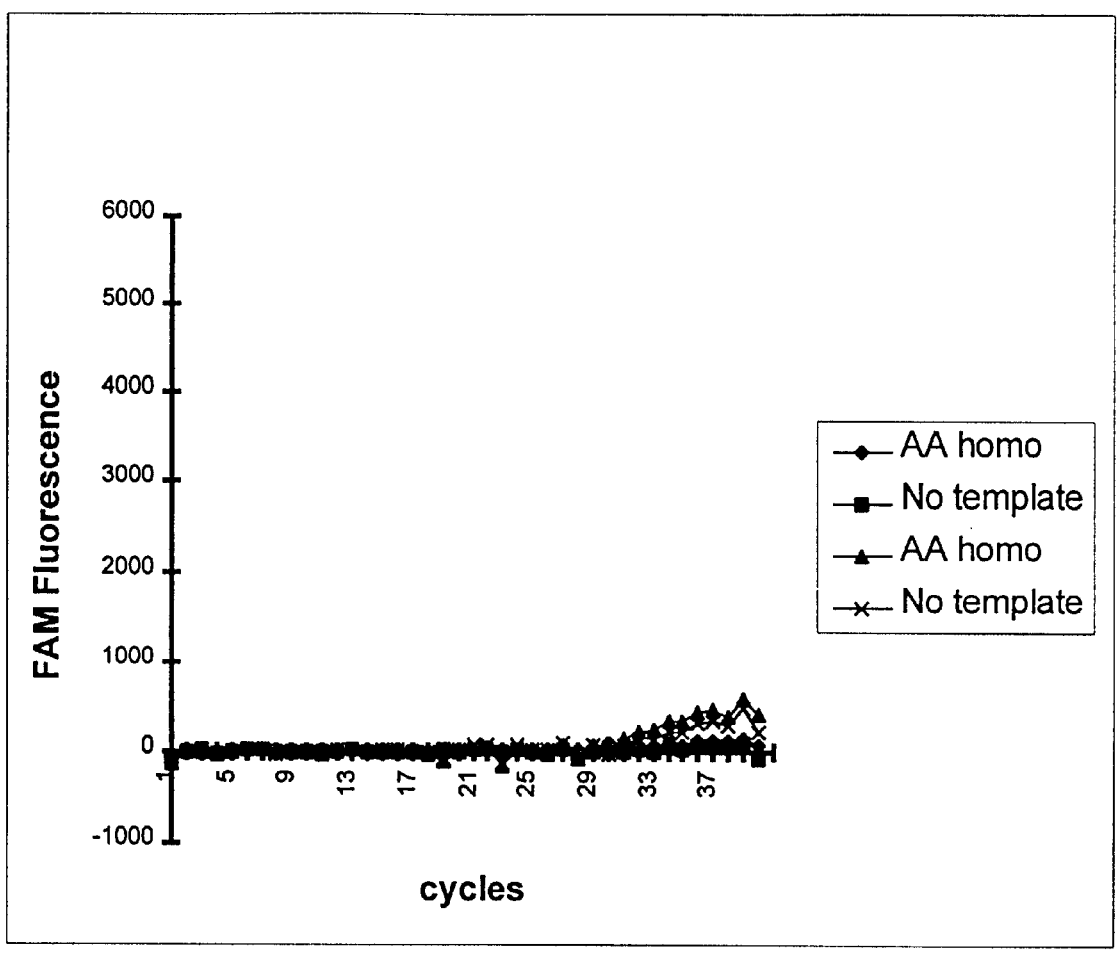
Figure 17B:
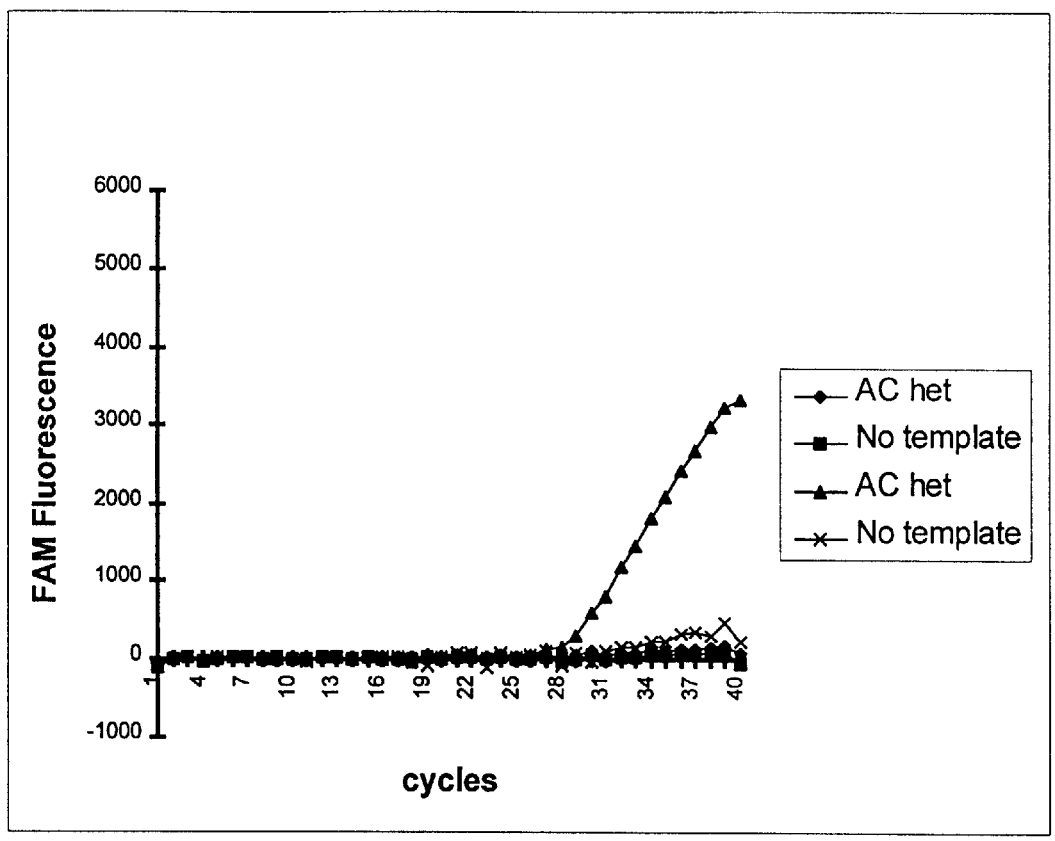
Figure 17C:
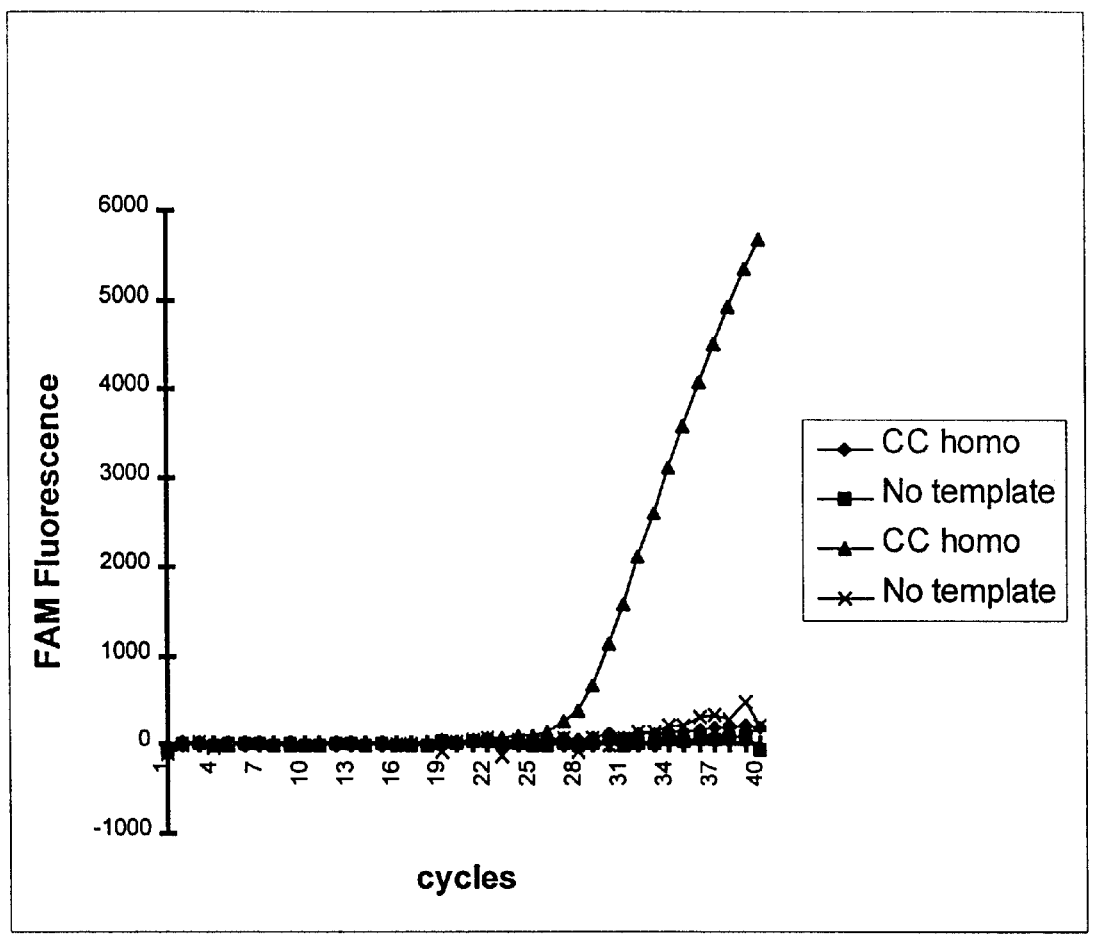

FIG. 17 shows a comparison between this invention and a bimolecular equivalent. In (a) mismatched targets show no appreciable amplification, in (b) and (c) a substantial allele specific signal is produced only by the matched Scorpions primers. In FIG. 17 results obtained using Scorpions primers are shown as triangles and crosses.

Figure 18:
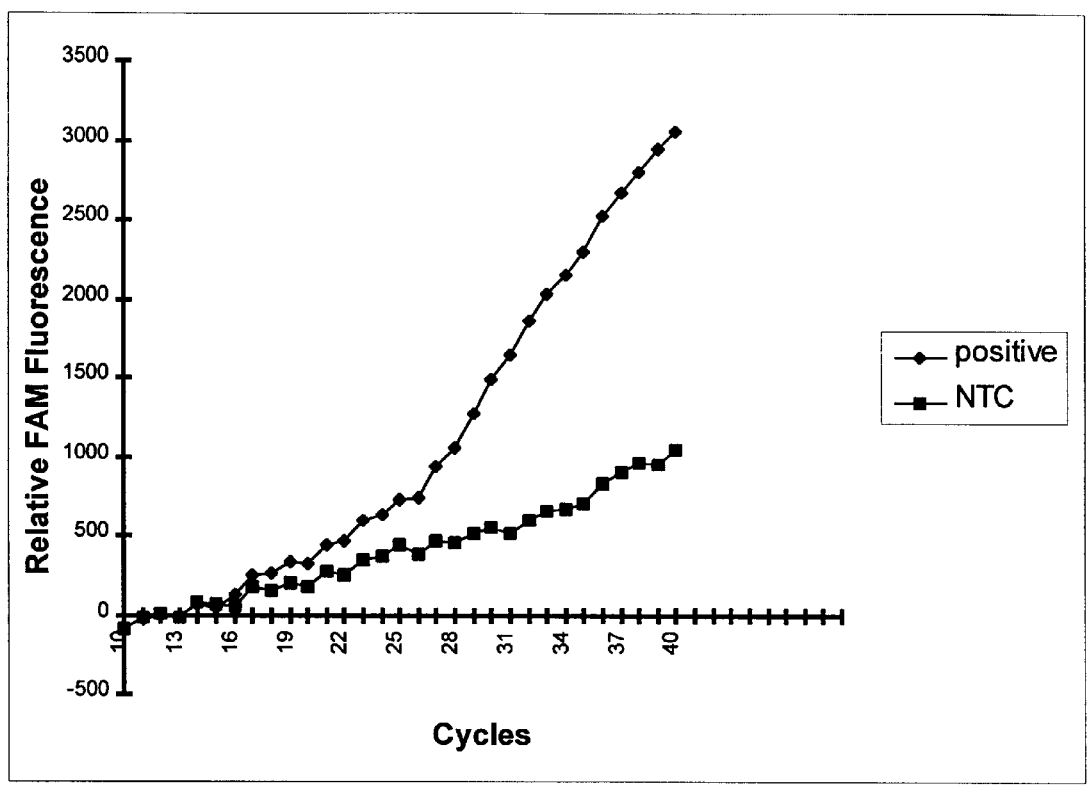

FIG. 18 shows use of the no quencher embodiment of the invention, fluorescent signal is generated upon hybridisation of a matched target binding region in contrast to a no-template control.

Figure 19:
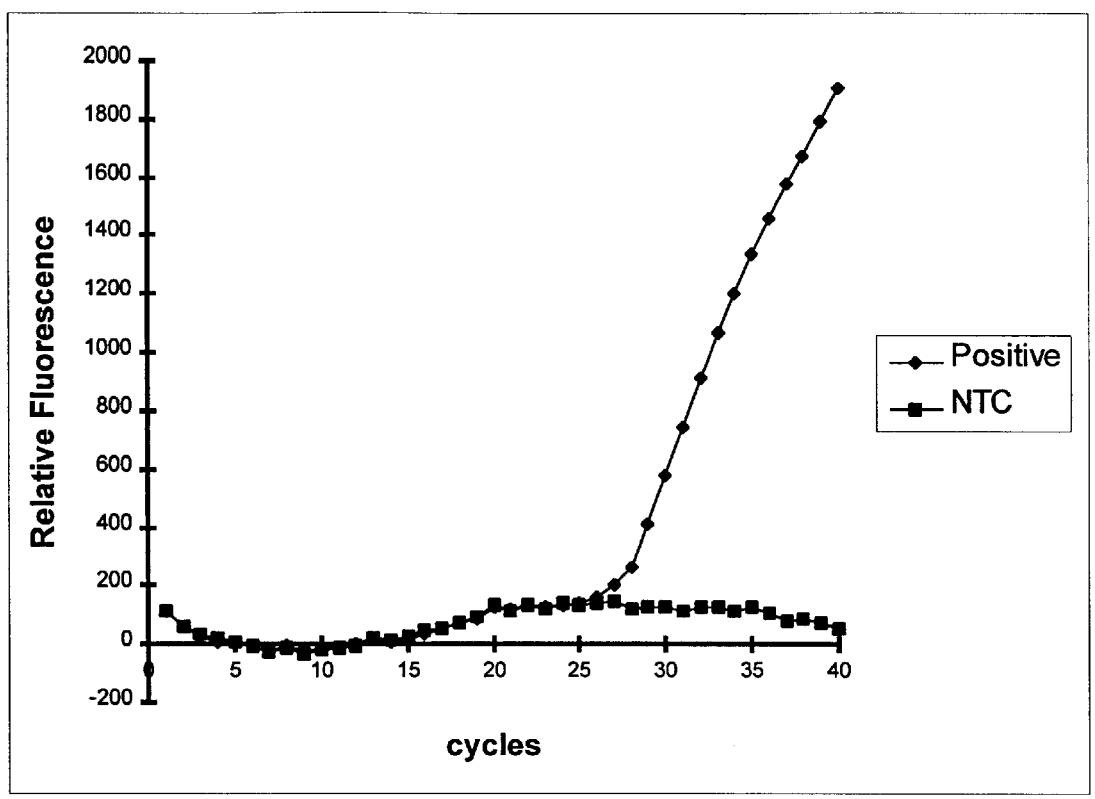
Figure 20A:
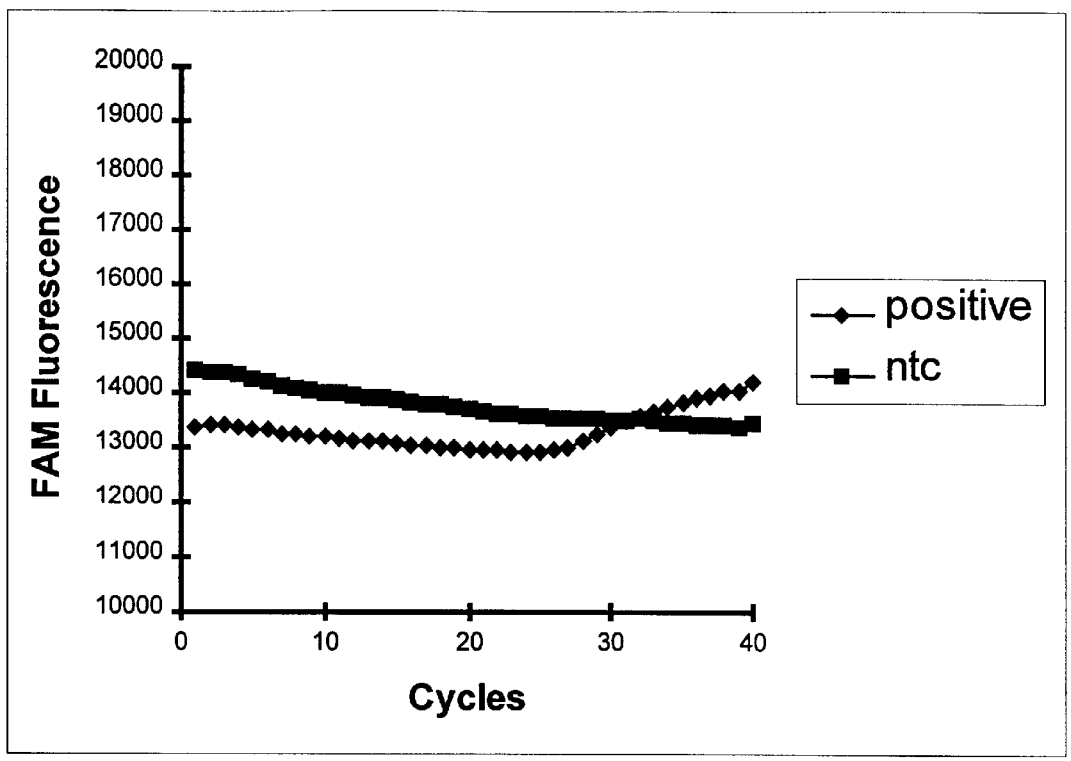
Figure 20B:
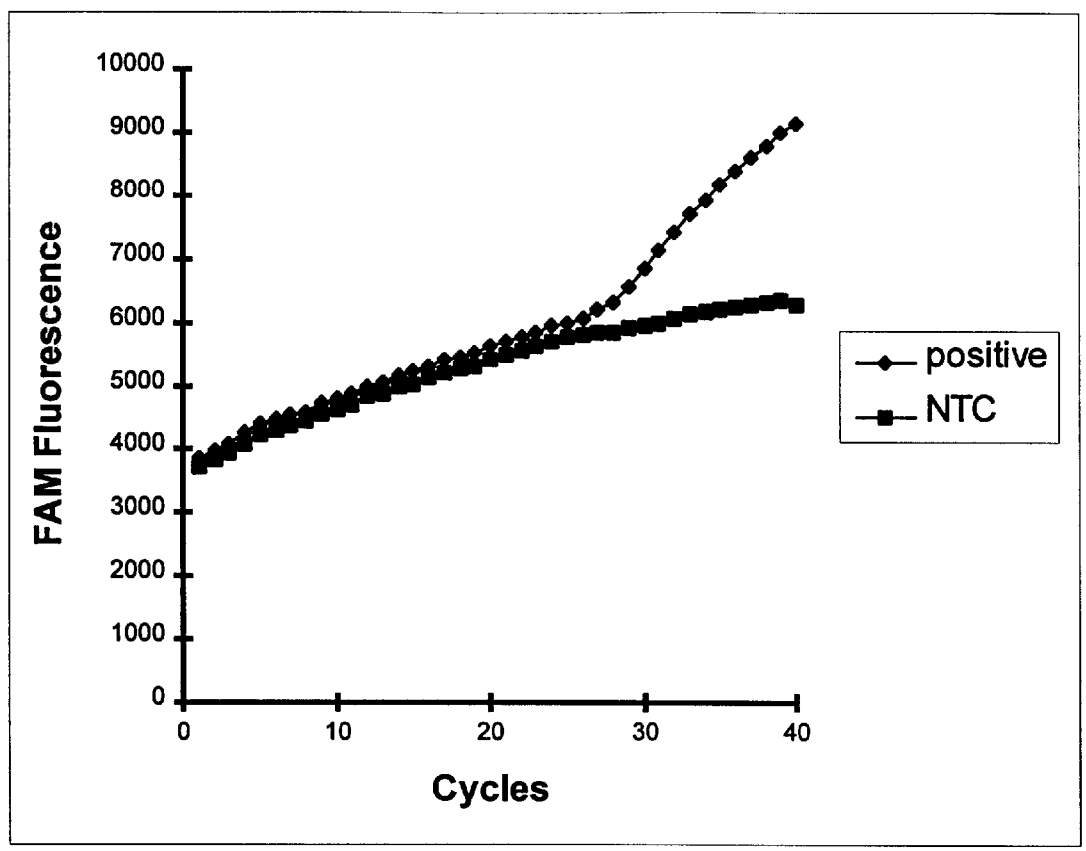
Figure 20C:
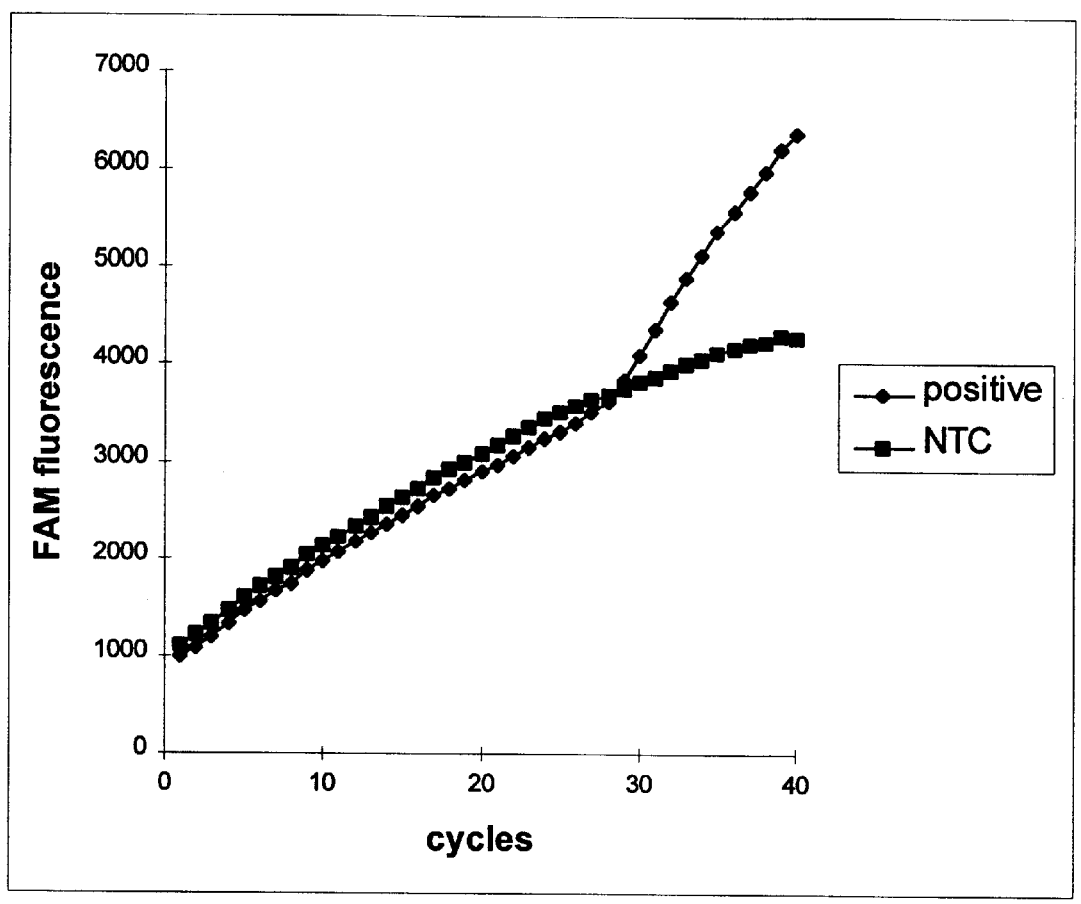
Figure 20D:
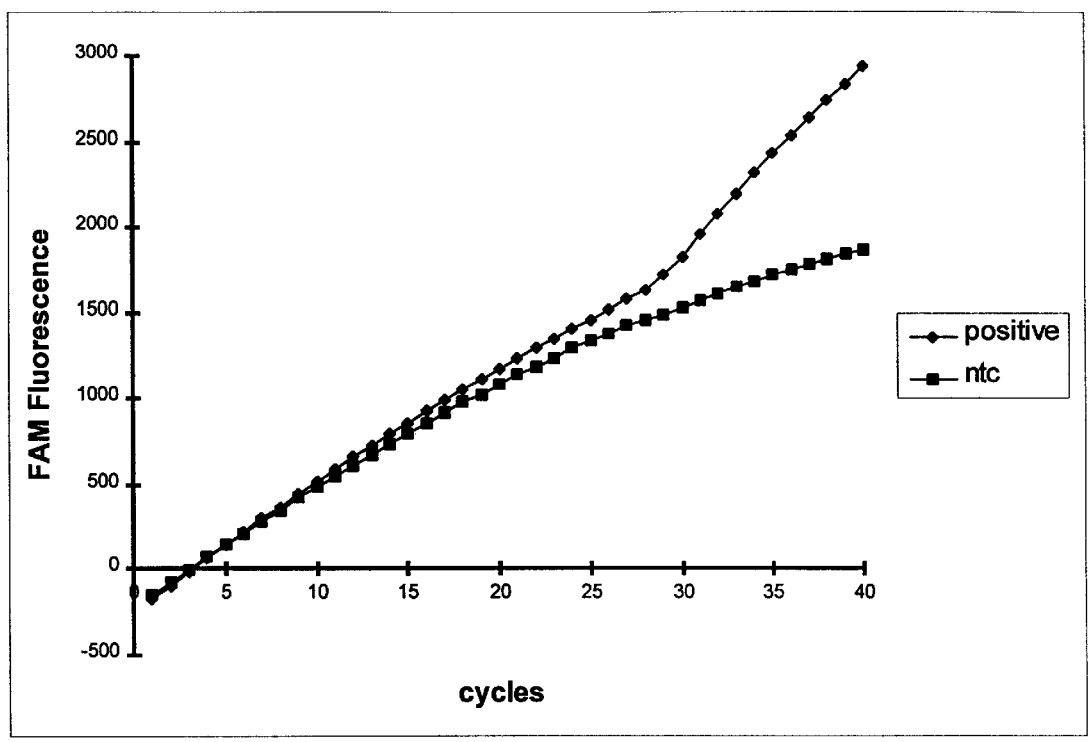

FIG. 19 shows that random coiling of a primer of the invention is sufficient to bring the fluorophore and quencher together.

FIG. 20 shows the bimolecular embodiment of the invention, different amounts of quencher oligonucleotide were added, (a) none, (b) 0.5 $\mu$M, (c) 2 $\mu$M and (d) 20 $\mu$M.

Figure 21A:
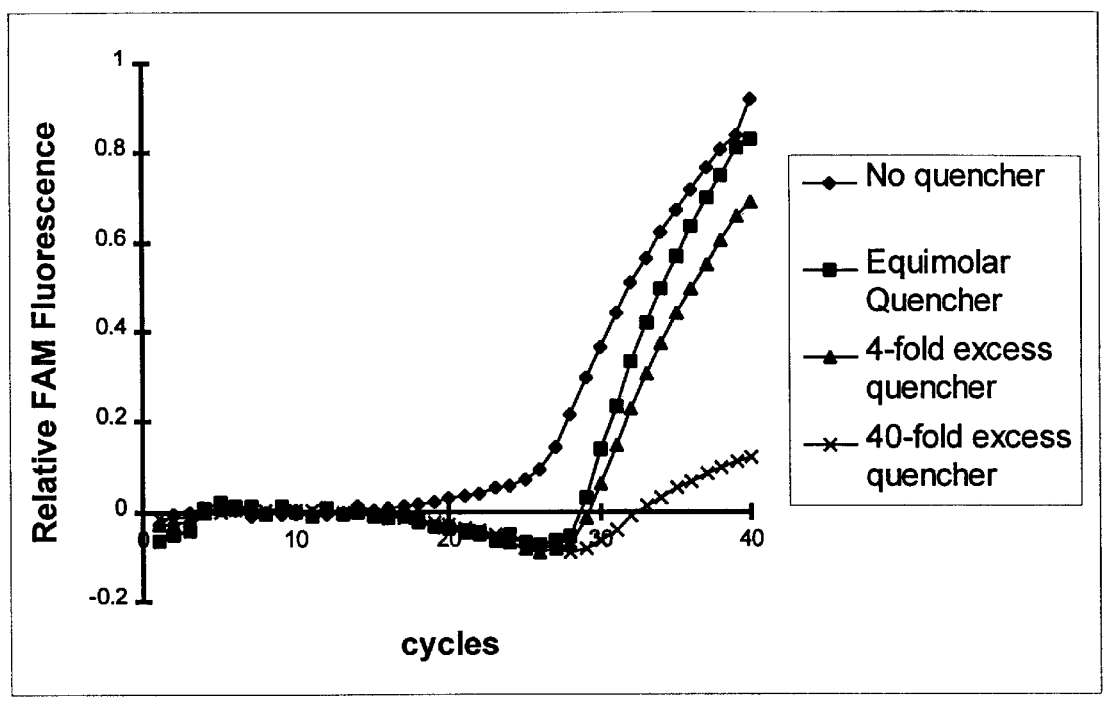
Figure 21B:
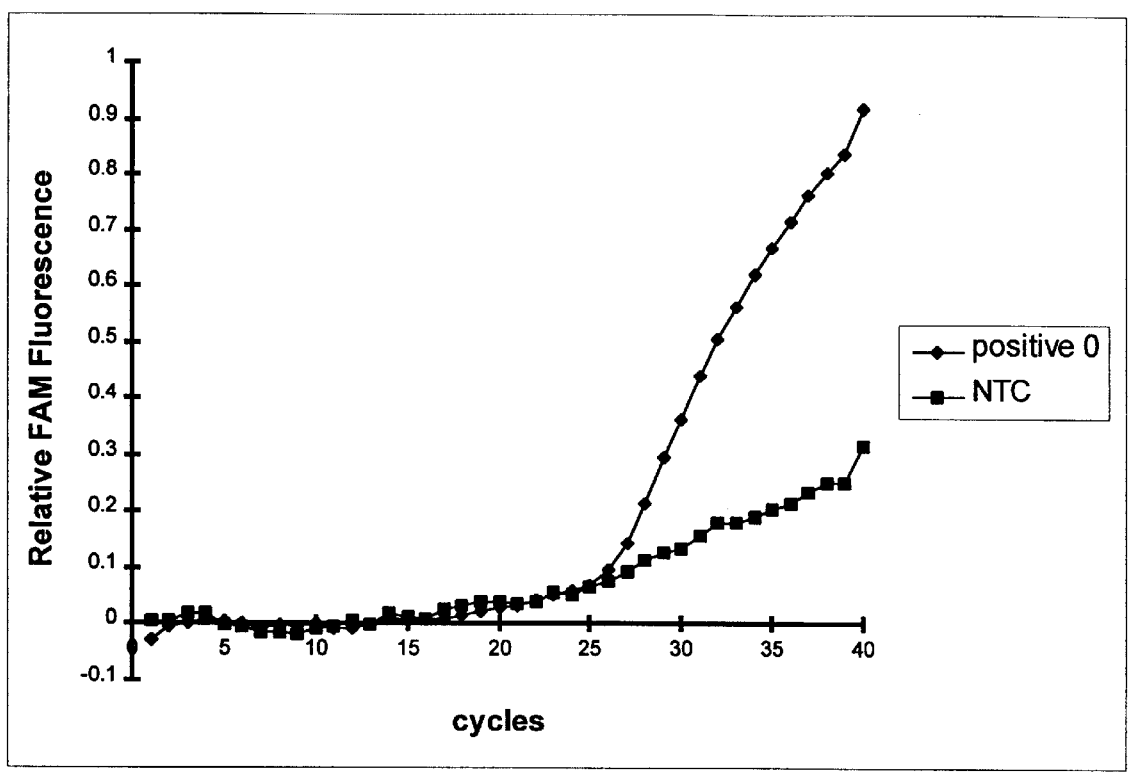

FIG. 21 shows (a) the proportion of free floating quencher to the Scorpions primer ie. 40X, 4X, 1X and 0X respectively, and (b) the effect of no quencher.

EXAMPLES

Materials

Primers/Scorpions Primers:

B2098-BRCA Scorpions: FAM-CGCACGATGTAGCACATCAGAA GCGTGCG-MR-HEG-TTGGAGATTTTGTCACTTCCA CTCTCAAA (SEQ ID NO:1) Underlined regions are the hairpin forming parts, FAM is the fluorescein dye, MR is a non-fluorogenic fluorophore attached to a uracil, HEG is the replication blocking hexethylene glycol monomer. The probe matches the "C-variant" of the BRCA2 polymorphism and mismatches the "A-variant".

R186–98: untailed equivalent of B2098: TTG-GAGATTTTGTCACTTCCACTCTCAAA (SEQ ID NO:2)

R187–98: opposing primer to the R186–98 and the equivalent Scorpions.

Z3702: the probe segment of the Scorpions B2098:
FAM-CGCACGATGTAGCACATCAGAA
  GCGTGCG-MR (SEQ ID NO:3)
Template DNA: previously genotyped DNA prepared by proteinase K and phenol/chloroform extraction was used at 50 ng per 50 µl reaction. Genotypes were typically one homozygous A/A, one homozygous C/C and one heterozygote (A/C).
Buffer (1×): 10 mM Tris-HCl (pH 8.3), 1.2 mM or 3.5 mM MgCl$_2$, 50 mM KCl, dNTPs (each at 100 µM), gelatin at 0.01% (w/v).
Enzyme: AmpliTaq Gold (Perkin-Elmer/ABI) was included in the reaction mix at 2units/50 µl reaction.

Example 1
Amplification Detected in Real Time

In order to monitor the performance of a Scorpions primer in an homogeneous amplification reaction, a PCR was performed using primers which flank a polymorphism in the BRCA2 gene. The target sequence selected had previously been used for allelic discrimination of the two variants but was too short for real time detection (the probe failed to hybridise at 60° C.—the lowest temperature in the thermocycling run). The (upper strand) probe entity was synthesised as part of a lower strand primer with a blocking HEG between the two functionalities. Target DNA could be selected to produce amplicon which would match or mismatch the probe.

Reaction conditions: After addition of template DNA, tubes were sealed and reactions were cycled under the following conditions: 20 min at 94° C. to activate the Amplitaq Gold; and 40 cycles of {94° C. for 45s, 60° C. for 45s}. Reactions were performed in an ABI PRISM 7700 fluorescence PCR machine.

Results: See FIG. 13. It is very clear that as amplicon accumulates, fluorescent signal is generated. There are several fluorescence readings at each timepoint and the sharp, stepwise nature of the signal increase reflects the rapid production of probe-target duplex in the early part of the thermocycle hold. This is due to the unimolecular mode of action of a Scorpion primer, which permits instantaneous recognition of an appropriate amplicon.

Example 2
Allelic Discrimination
Materials and methods as above.

Results: See FIG. 14. In this experiment, the probe matched or mismatched the amplicons at the polymorphic base. Both amplifications were equally efficient (as viewed by agarose gels [results not shown]), but the matched product was detected much more readily than the mismatched. This illustrates the strong specificity of the system even down to a single base change in the amplicon.

Example 3
Primer Titration

Materials and method, see above. Titration of the primer B2098 with its untailed equivalent (R186–98) was from 100% Scorpions to 10% Scorpions; total primer was constant at 500 nM.

Results: See FIG. 15. At all ratios of Scorpions:untailed primer, reactions were clearly detectable on the ABI7700. Indeed, the Ct (the point at which signal crosses a threshold above "background") was identical regardless of the ratio of Scorpions to untailed primer indicating the same levels of priming effieciency throughout the series. The only variable was absolute fluorescence signal (as would be expected). The efficiency of this system is in marked contrast to available methods where higher concentrations of probe are required to drive kinetically the bimolecular probing event.

Example 4
Endpoint Readings

Materials and methods: Reactions were set up as above but were carried out at two different magnesium concentrations (1.2 and 3.5 mM). DNAs of all three genotypes and a no template control (NTC) were used and the fluorescence was measured before and after amplification. Fluorescence numbers are the means of at least 6 separate readings from duplicate samples.

Results

| Sample | CC | | AC | | AA | | NTC | |
|---|---|---|---|---|---|---|---|---|
| Mg | 1.2 | 3.5 | 1.2 | 3.5 | 1.2 | 3.5 | 1.2 | 3.5 |
| Before | 6396 | 3706 | 5700 | 2958 | 6157 | 3299 | 6257 | 3685 |
| After | 12144 | 10316 | 8614 | 6140 | 6818 | 4641 | 6616 | 4453 |
| Change | 5748 | 6610 | 2914 | 3182 | 661 | 1342 | 359 | 768 |

Fluorescence readings increased through the PCR in a target dependent manner. In fact the signals generated for heterozygotes are approximately half those for the CC homozygotes and this may be useful for genotyping in a simple way or for analysis of heteroplasmy where the allele ratios vary more widely than 100:0, 50:50 or 0:100. In addition, the signals generated for mismatch targets were similar to background levels showing that although amplification had occurred, the probe was not efficiently hybridising unless there was a perfect match. Increasing the magnesium concentration decreased this discrimination but also ensured that the backgrounds were lower, presumably by promoting hybridisation in general.

In addition to observing these signal changes by fluorimeter, increased fluorescence could be detected by visual inspection of the tubes backlit by UV transilluminator. This is a remarkable observation since the FAM dye has an excitation optimum at ~490 nm whereas the UV box illuminates at ~330–360 nm. This means that the fluorescent yield was far from optimal and may be substantially improved by the use of more appropriate wavelengths.

Example 5
Analysis of Heteroplasmy by Scorpions

Reactions were set up as in Example 4, but template DNA was a standard quantity with varying admixtures of C homozygote to A homozygote: 100%:0%, 90:10, 50:50, 10:90, 0:100 and NTC. After 40 cycles of PCR, the FAM fluorescence readings were taken and the NTC subtracted from each. The data are shown in FIG. 16.

Example 6
Comparative Performance of Scorpions

In order to examine the relative performance of Scorpions versus a bimolecular equivalent, the same amplicon and probe sequences were used in each format. The bimolecular format constituted 500 nM each of primers R186–98 and R187–98, plus 500 nM Molecular Beacon Z3702, while the unimolecular version contained B2098 and R187–98 each at 500 nM. Other reaction constituents were identical to previous experiments (with 1.2 mM Mg) and cycling was for 40 cycles as above. The results of these amplifications in real time with targets which are homozygous C, homozygous A, or heterozygous A/C are shown in FIG. 17. Clearly, there was no substantial amplification above background for the reactions with a bi-molecular probing mode of action, whereas substantial allele specific signals were produced in the Scorpions reactions. It is worth noting that the final level of signal for the heterozygote was half that generated by the homozygous C amplification. This experiment illustrates the substantial kinetic advantages of the unimolecular hybridisation approach of this invention.

Examples 7 and 8
Random Coil Embodiment and Bimolecular Embodiment
Scorpion B2731:
fam-AGGTAGTGCAGAGAGTG-mr-h-GAGCCTCAACATCCTGCTCCCCTCCTACTAC (SEQ ID NO:4)
Scorpion B4249 (no quencher on same molecule)
fam-AGGTAGTGCAGAGAGTG-h-GAGCCTCAACATCCTGCTCCCCTCCTACTAC (SEQ ID NO:5)
Quencher oligonucleotide (complement of the tail of B4249):
CACTCTCTGCACTACCT-mr (SEQ ID NO:6)
ARMS primer R284-97: TTCGGGGCTCCACACGGC-GACTCTCAAC (SEQ ID NO:7)
ARMS primer R283-97: TTCGGGGCTCCACACGGC-GACTCTCAAG (SEQ ID NO:8)
Target is the H63D polymorphism of the human hereditary haemochromatosis gene (HH), B2731 and B4249 are "common" primers to oppose the ARMS primers R283-97, R283-97. Cycling conditions and reaction composition as above. Primers (including Scorpion primers) were used at 500 nM concentration.

For the two molecule example, the quencher oligonucleotide was incorporated at 0, 0.5 2 and 20 mM, that is: 0, 1, 4, 40 fold relative to the Scorpion primer.

The random coil embodiment (FIG. 19) confirms that random coiling alone can be sufficient to bring the probe and quencher together and that an increase in signal is readily obtained in continuous monitoring of PCR. (Furthermore, it should be noted that this particular amplicon had previously proven refractory to probing in a TaqMan or Molecular Beacons assay).

The bimolecular embodiment also gave good results (see FIGS. 20 and 21). The more quencher was added, the lower the backgrounds in the absence of amplicon. The optimal overall performance (taking account of absolute signal strength and signal/noise) was with equimolar and 4× excess quencher.

Example 9
No Quencher Embodiment
Scorpion B4249 (no quencher)
fam-AGGTAGTGCAGAGAGTG-h GAGCCTCAACATC-CTGCTCCCCTCCTACTAC (SEQ ID NO:5)
ARMS primer R284-97
TTCGGGGCTCCACACGGCGACTCTCAAC (SEQ ID NO:7)

Reactions were set up as described in the previous examples. Primers were included at 50 nM. The target was the H63D mutation of the human hereditary haemochromatosis gene (HH). 25 ng of DNA was added per reaction. B4249 was the common primer in combination with the ARMS mutant primer R284-97. Cycling was as described in the previous examples. The results are shown in FIG. 18.

In this example, mutation specific signal was generated in the absence of a quencher. Random folding of the Scorpion primer around the fluorophore provides sufficient quenching of the fluorophore. An increase in signal is readily obtained during continuous monitoring of PCR.

What is claimed is:

1. A method for the detection of a target nucleic acid, which method comprises:
   (a) bringing together in a nucleic acid hybridization medium (i) nucleic acid from a sample, said nucleic acid comprising a template nucleic acid sequence and a target nucleic acid sequence, and (ii) a tailed nucleic acid primer comprising, in 5' to 3' order, a template binding region and a tail comprising a linker and a target binding region, in the presence of appropriate nucleoside triphosphates and an agent for polymerization thereof, under conditions such that the template binding region of the primer will hybridize to a complementary sequence in the template nucleic acid and be extended to form a primer extension product, the tail of the nucleic acid primer remaining uncopied during amplification, and
   (b) separating any said product from the template, whereupon the target binding region in the tail of the primer will hybridize to a sequence in the primer extension product complementary to the target nucleic acid, and wherein any such target specific hybridization is detected via a detectable change in a signalling system, such that the presence or absence of the target nucleic acid in the sample is detected by reference to the presence or absence of a detectable change in the signalling system.

2. A method as claimed in claim 1 wherein the tailed nucleic acid primer is used as an amplification primer in an amplification system.

3. A method as claimed in claim 2 wherein the amplification system is the polymerase chain reaction (PCR).

4. A method as claimed in claim 2 or 3 wherein the linker in the tail comprises a blocking moiety to prevent copying of the tail.

5. A method as claimed in claim 4 wherein the tail of the nucleic acid primer comprises a non-copiable species.

6. A method as claimed in claim 1, 2 or 3 wherein hybridisation of the tailed primer to template nucleic acid is performed at a stringency so as to allow primer extension on related template sequences.

7. A method as claimed in claim 6 wherein the related template sequences are human leukocyte antigen (HLA) sequences.

8. A method as claimed in claim 1, 2 or 3 wherein hybridisation of the template binding region and/or target binding region of the primer to a complementary sequence is allele specific.

9. A method as claimed in claim 1, 2 or 3 and using more than one nucleic acid primer for the detection of more than one target nucleic acid sequence.

* * * * *

UNITED STATES PATENT AND TRADEMARK OFFICE
CERTIFICATE OF CORRECTION

PATENT NO. : 6,326,145 B1  
APPLICATION NO. : 09/200232  
DATED : December 4, 2001  
INVENTOR(S) : Whitcombe et al.

It is certified that error appears in the above-identified patent and that said Letters Patent is hereby corrected as shown below:

Col. 19, approx. lines 28-55, should read as corrected:
    1. A method for the detection of a target nucleic acid, which comprises:

a) bringing together in a nucleic acid hybridization medium (i) nucleic acid from a sample, said nucleic acid comprising a template nucleic acid sequence and a target nucleic acid sequence, and (ii) a tailed nucleic acid primer comprising, in ~~5' to 3'~~ 3' to 5' order, a template binding region and a tail comprising a linker and a target binding region, in the presence of appropriate nucleoside triphosphates and an agent for polymerization thereof, under conditions such that the template binding region of the primer will hybridize to a complementary sequence in the template nucleic acid and be extended to form a primer extension product, the tail of the nucleic acid primer remaining uncopied during amplification, and (b) separating any said product from the template, whereupon the target binding region in the tail of the primer will hybridize to a sequence in the primer extension product complementary to the target nucleic acid, and wherein any such target specific hybridization is detected via a detectable change in a signalling system, such that the presence or absence of the target nucleic acid in the sample is detected by reference to the presence or absence of a detectable change in the signalling system.

Signed and Sealed this

Thirty-first Day of October, 2006

JON W. DUDAS  
*Director of the United States Patent and Trademark Office*